(12) United States Patent
Momoki et al.

(10) Patent No.: US 11,026,629 B2
(45) Date of Patent: Jun. 8, 2021

(54) BIOLOGICAL INFORMATION DETECTION DEVICE

(71) Applicant: TERUMO KABUSHIKI KAISHA, Tokyo (JP)

(72) Inventors: Hideyuki Momoki, Hadano (JP); Yasuhiro Kobayashi, Sendai (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 359 days.

(21) Appl. No.: 16/003,507

(22) Filed: Jun. 8, 2018

(65) Prior Publication Data

US 2018/0289329 A1 Oct. 11, 2018

Related U.S. Application Data

(63) Continuation of application No. PCT/JP2016/085582, filed on Nov. 30, 2016.

(30) Foreign Application Priority Data

Jan. 29, 2016 (JP) .............................. JP2016-016217

(51) Int. Cl.
*A61B 5/1486* (2006.01)
*A61B 5/1459* (2006.01)
(Continued)

(52) U.S. Cl.
CPC .......... *A61B 5/6849* (2013.01); *A61B 5/1459* (2013.01); *A61B 5/1473* (2013.01);
(Continued)

(58) Field of Classification Search
CPC ... A61B 5/6849; A61B 5/1459; A61B 5/1473; A61B 5/1486; A61B 5/6866;
(Continued)

(56) References Cited

U.S. PATENT DOCUMENTS 5,971,963 A 10/1999 Choi
6,058,321 A 5/2000 Swayze et al.
(Continued)

FOREIGN PATENT DOCUMENTS

CN 104168826 A 11/2014
JP 5161341 B2 3/2013
(Continued)

OTHER PUBLICATIONS

Office Action dated May 21, 2020 in corresponding Chinese Patent Application No. 201680071908.9.
(Continued)

*Primary Examiner* — Navin Natnithithadha
(74) *Attorney, Agent, or Firm* — Foley & Lardner LLP

(57) ABSTRACT

A biological information detection device includes: a needle body configured to pierce the living body; and a sensor that has an elongated shape and is configured to detect biological information using a distal end portion of the sensor that is configured to indwell inside a living body. The distal end portion of the sensor is insertable into the living body by moving along the needle body after the needle body has pierced the living body.

14 Claims, 20 Drawing Sheets

(51) Int. Cl.
*A61B 5/1473* (2006.01)
*A61B 5/145* (2006.01)
*A61B 5/00* (2006.01)

(52) U.S. Cl.
CPC .......... *A61B 5/1486* (2013.01); *A61B 5/6886* (2013.01); *A61B 5/14532* (2013.01); *A61B 5/14539* (2013.01); *A61B 5/14546* (2013.01); *A61B 2560/063* (2013.01)

(58) Field of Classification Search
CPC ............ A61B 5/14532; A61B 5/14539; A61B 5/14546; A61B 2560/063
USPC .......................................... 600/309, 342–366
See application file for complete search history.

(56) References Cited

U.S. PATENT DOCUMENTS

| | | | |
|---|---|---|---|
| 2010/0174163 | A1 | 7/2010 | Brister et al. |
| 2011/0319729 | A1* | 12/2011 | Donnay ............. A61B 5/15087 600/309 |
| 2013/0296677 | A1 | 11/2013 | Pryor et al. |
| 2015/0119662 | A1 | 4/2015 | Larson et al. |
| 2016/0066953 | A1* | 3/2016 | Minamiguchi ...... G01N 21/645 600/317 |

FOREIGN PATENT DOCUMENTS

| | | |
|---|---|---|
| JP | 2013-523216 A | 6/2013 |
| WO | WO-2005/044116 A2 | 5/2005 |
| WO | WO-2011/119896 A1 | 9/2011 |
| WO | WO-2014/162383 A1 | 10/2014 |
| WO | WO-2014/185067 A1 | 11/2014 |
| WO | WO-2015/061593 A1 | 4/2015 |
| WO | WO-2016/143234 A1 | 9/2016 |

OTHER PUBLICATIONS

International Search Report with English language translation and Written Opinion issued in International Application No. PCT/JP2016/085582 dated Feb. 21, 2017.
Office Action dated Sep. 15, 2020 in corresponding Japanese Patent Application No. 2017-5637192015.

* cited by examiner

FIG. 2A 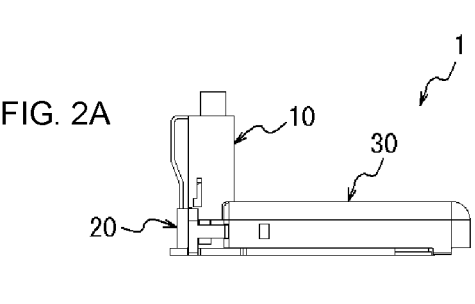 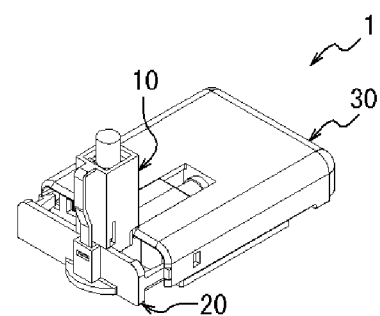
FIG. 2B 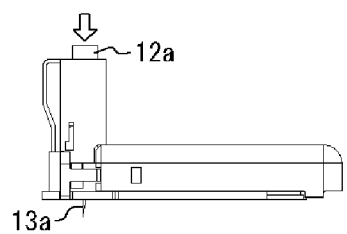 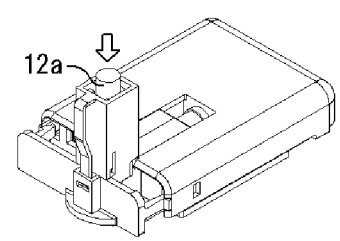
FIG. 2C 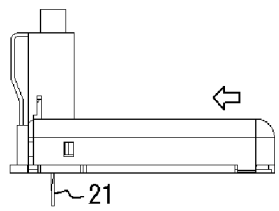 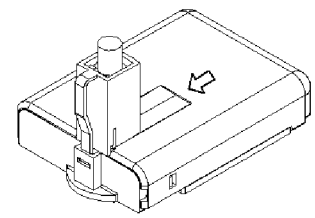
FIG. 2D 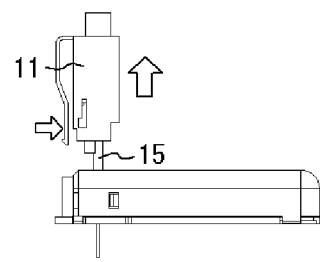 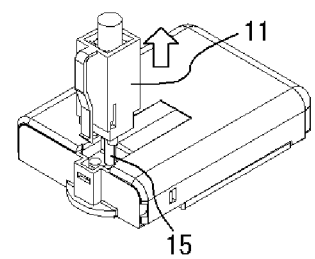
FIG. 2E  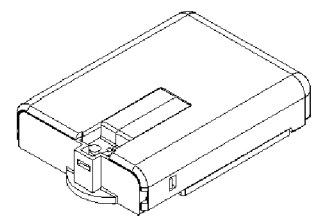

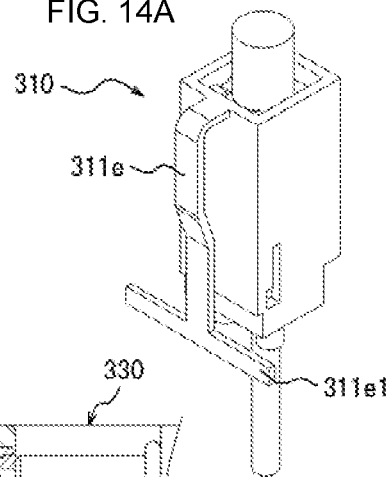
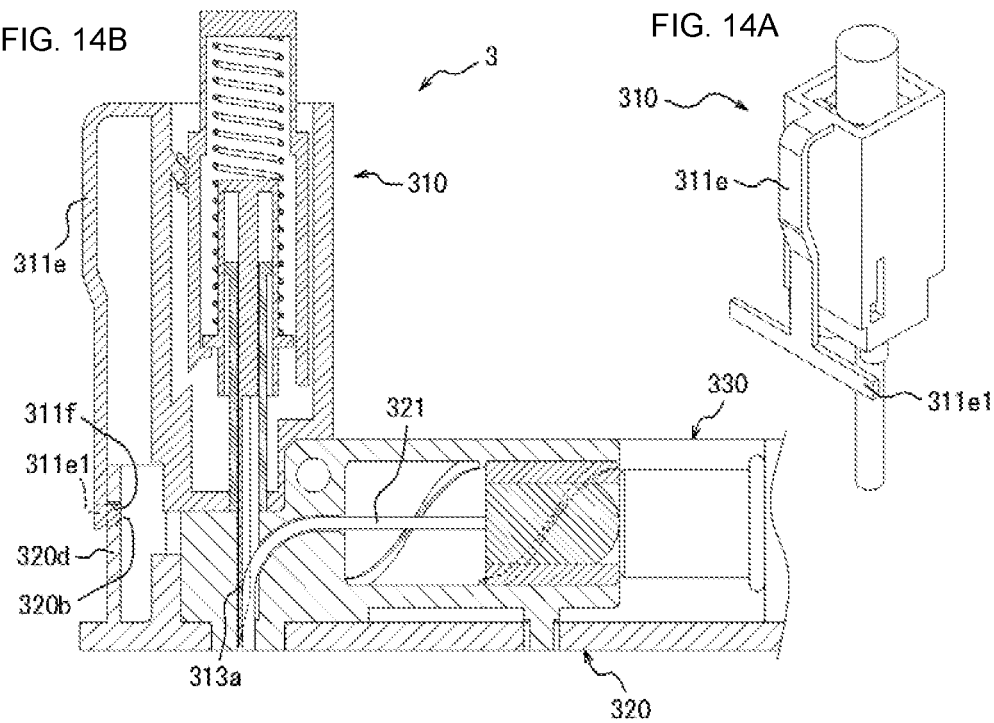
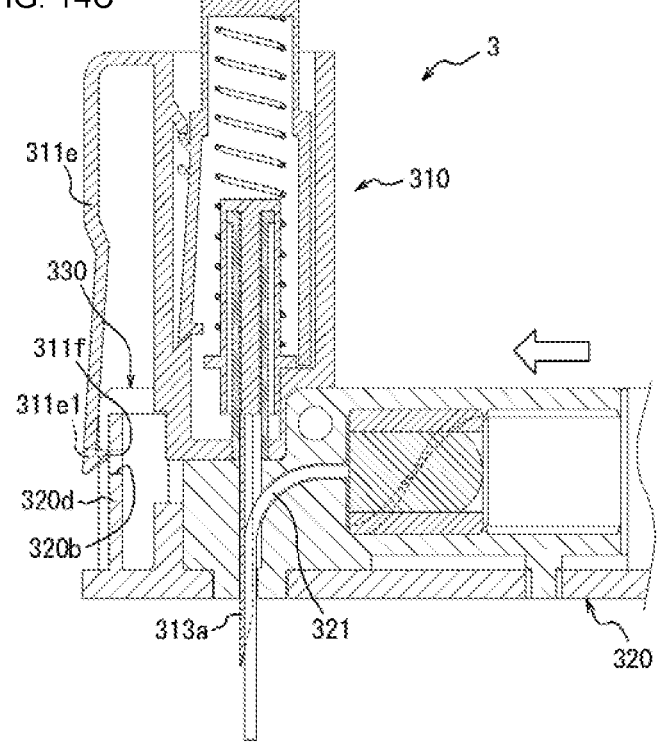

FIG. 16A
FIG. 16B
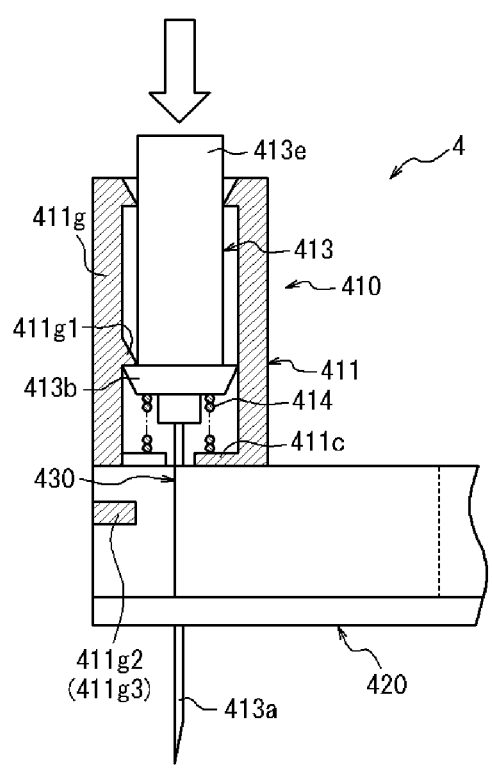
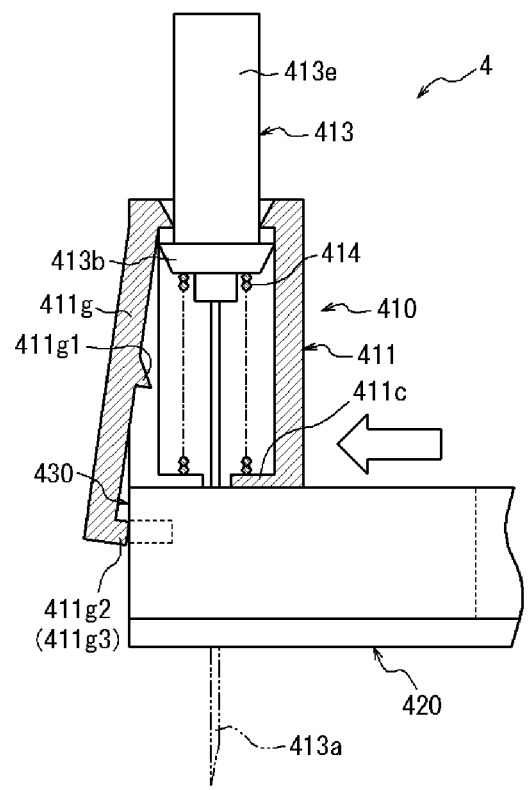

BIOLOGICAL INFORMATION DETECTION DEVICE

CROSS-REFERENCE TO RELATED APPLICATIONS

The present application is a bypass continuation of PCT Application No. PCT/JP2016/085582, filed on Nov. 30, 2016, which claims priority to Japanese Application No. 2016-016217, filed on Jan. 29, 2016. The contents of these applications are hereby incorporated by reference in their entireties.

BACKGROUND

The present disclosure relates to a biological information detection device that includes a sensor configured to detect biological information and a needle body configured to pierce a living body in order to insert a distal end portion of the sensor into the living body, and particularly, to a device that enables the distal end portion of the sensor to be inserted into the living body to a desired depth with a simple configuration.

Conventionally, devices that cause a sensor to indwell in a subcutaneous tissue for several days are used, for example, in order to measure a glucose concentration in an intertissue fluid of a diabetic. For example, Japanese Patent No. 5161341 describes a biological information detection device configured to detect biological information including the concentration of an analyte (substance) to be detected (for example, glucose, pH, cholesterol, proteins, or the like) in a living body (for example, a person to be measured, such as a diabetic).

The biological information detection device described in Patent Literature 1 includes a sensor that has an elongated shape and enables detection of biological information by causing a distal end portion to indwell inside a living body, and a needle body that pierces the living body to insert the distal end portion of the sensor into the living body.

SUMMARY

However, in Japanese Patent No. 5161341, because the needle body housing the sensor is inserted into the living body together with the sensor in the conventional biological information detection device, it is difficult to cause the sensor to indwell at a desired depth even if the needle body is inserted to a desired depth when a position of the sensor deviates within the needle body at the time of puncture or the sensor also moves along with the needle body withdrawn at the time of removal. Therefore, it is required to provide a mechanism configured to fix a position of the sensor inside the needle body at the time of puncture and to fix a position of the sensor inside the living body during removing the needle so that there is a problem that the configuration becomes complicated.

The present disclosure has been developed in order to solve the above-described issue, and an object of certain embodiments of the present disclosure is to provide a biological information detection device configured to cause a distal end portion of a sensor to indwell at a desired depth in a living body with a simple configuration.

According to one embodiment, a biological information detection device includes: a sensor that has an elongated shape and enables detection of biological information by causing a distal end portion to indwell inside a living body; and a needle body that pierces the living body to insert the distal end portion of the sensor into the living body, the biological information detection device capable of inserting the distal end portion of the sensor into the living body along the needle body piercing the living body.

In one aspect, a proximal end portion of the sensor is movable in a direction different from an extending direction of the needle body.

In one aspect, the proximal end portion of the sensor is movable in a direction along a surface of the living body.

In one aspect, the sensor has a measurement light emitting portion that is arranged at the distal end portion of the sensor and generates light, and a light guide portion that transmits the light from the measurement light emitting portion to the proximal end portion of the sensor.

In one aspect, the biological information detection device includes an end member that is fixed to the proximal end portion of the sensor and allows at least light from the proximal end portion of the sensor to pass therethrough, and the end member has a light adjustment portion that collects light diffused from the proximal end portion of the sensor.

In one aspect, the light adjustment portion collects the light diffused from the proximal end portion of the sensor so as to become collimated light.

In one aspect, the biological information detection device includes: an end member that is fixed to the proximal end portion of the sensor and allows at least a signal corresponding to concentration of an analyte to be detected obtained from the sensor to pass therethrough; a base member that is affixable to the surface of the living body; an end member guide path provided that is provided in the base member and guides the end member; and a detector that has a reception unit receiving the signal from the end member and a detection unit detecting the concentration of the analyte to be detected based on the signal received by the reception unit, and that the detector be attachable or detachable to or from the base member.

In one aspect, the distal end portion of the sensor is inserted into the living body along the needle body by pushing and moving the end member by the detector.

In one aspect, as the end member is pushed and moved by the detector, the end member rotates in accordance with the movement.

In one aspect, the end member guide path has a cylindrical inner peripheral surface to accommodate the end member, and the inner peripheral surface of the end member guide path an outer peripheral surface of the end member be connected via a screw portion that rotates the end member in accordance with the movement of the end member.

In one aspect, the end member guide path has a cylindrical inner peripheral surface to accommodate the end member, the end member has a cylindrical outer peripheral surface, the detector has an insertion tube portion having a cylindrical outer peripheral surface insertable into the end member guide path and an operation portion integrally rotatable with the insertion tube portion, the inner peripheral surface of the end member guide path and the outer peripheral surface of the insertion tube portion are connectable via a screw portion that moves the insertion tube portion toward a depth of the end member guide path in accordance with a rotational operation of the operation portion, and a distal end surface of the insertion tube portion and a proximal end surface of the end member are connectable via a fitting portion that inhibits mutual rotation.

In one aspect, the base member is provided with a sensor guide path that guides the sensor, the sensor guide path is gradually curved toward the surface of the living body as approaching the needle body, and a reversely curved guide portion, which guides the sensor to be curved in a direction opposite from a curved direction of the sensor guide path, is provided in the sensor guide path on a side close to the needle body.

In one aspect, the needle body is insertable in the living body by moving the detector with respect to the base member, and the end member is pushed and moved by further moving the detector so that the distal end portion of the sensor is inserted into the living body along the needle body.

In another embodiment, the biological information detection device includes: a puncturing needle holding member that holds the needle body; a puncturing biasing member that biases the puncturing needle holding member toward the surface of the living body; and a puncturing movable portion that is engaged with the puncturing needle holding member to hold a state in which the puncturing needle holding member receives a biasing force from the puncturing biasing member, and that the puncturing movable portion be released from engagement with the puncturing needle holding member by being pushed by the detector as the detector is moved with respect to the base member.

In one aspect, the biological information detection device includes a puncture unit that holds the needle body and is detachable from the base member, and that the puncture unit be detachable from the base member when the detector is moved with respect to the base member and insertion of the distal end portion of the sensor into the living body is completed.

In one aspect, the puncture unit further includes a detachment-inhibiting movable portion that is engaged with the base member to inhibit detachment of the puncture unit from the base member, and the detachment-inhibiting movable portion be released from engagement with the base member by being pushed by the detector when insertion of the distal end portion of the sensor into the living body is completed.

In one aspect, the needle body is removed from the living body when the detector is moved with respect to the base member and insertion of the distal end portion of the sensor into the living body is completed.

In one aspect, the biological information detection device includes: a removing needle holding member that holds the needle body; a removing biasing member that biases the removing needle holding member in a direction to be removed from the living body; and a removing movable portion that is engaged with the removing needle holding member to hold a state in which the removing needle holding member receives a biasing force from the removing biasing member, and the removing movable portion be released from engagement with the removing needle holding member by being pushed by the detector when insertion of the distal end portion of the sensor into the living body is completed.

According to certain embodiments of the present disclosure, the sensor can be inserted into the living body separately from the needle body, and thus, the distal end portion of the sensor can indwell at a desired depth in the living body. In addition, according to certain embodiments of the present disclosure, it is unnecessary to provide the mechanism configured to fix the sensor at the time of puncture and removal, which is conventionally required.

Therefore, according to certain embodiments of the present disclosure, it is possible to provide the biological information detection device capable of causing the distal end portion of the sensor to indwell at a desired depth in the living body with the simple configuration.

BRIEF DESCRIPTION OF THE DRAWINGS

FIGS. 2A-2E are views for describing use of the biological information detection device of FIG. 1, in which FIG. 2A illustrates a state at the time of affixing to a living body surface, FIG. 2B illustrates a state at the time of puncture, FIG. 2C illustrates a state at the time of inserting the sensor, FIG. 2D illustrates a state at the time of removing a needle body, and FIG. 2E illustrates a state at the time of measurement.

FIGS. 7A and 7B are views illustrating a modified example of the biological information detection device of FIG. 1, in which FIG. 7A is a perspective view, and FIG. 7B is a right side view.

FIGS. 11A-11D are schematic views illustrating a biological information detection device according to a second embodiment of the present disclosure, in which FIG. 11A is a left side view, FIG. 11B is a front view, FIG. 11C is a right side view, and FIG. 1DB is a cross-sectional view taken along a line A-A of FIG. 11B.

FIGS. 13A and 13B are cross-sectional views illustrating states before and after puncture of the biological information detection device of FIGS. 11A-11D according to FIG. 12A, in which FIG. 13A illustrates the state before puncture, and FIG. 13B illustrates the state after puncture.

FIGS. 14A-14C are views illustrating a biological information detection device according to a third embodiment of the present disclosure, in which FIG. 14A is a perspective view of a puncture unit, FIG. 14B is a partial cross-sectional side view illustrating a state before inserting the sensor as viewed from the right side, and FIG. 14C is a partial cross-sectional side view illustrating a state at the time of completing insertion of the sensor as viewed from the right side.

FIGS. 15A and 15B are schematic views illustrating a biological information detection device according to a fourth embodiment of the present disclosure, in which FIG. 15A is a front view illustrating a state before puncture, and FIG. 15B is a partial cross-sectional side view illustrating the state before puncture as viewed from right side.

FIGS. 16A and 16B are schematic views illustrating the biological information detection device of FIGS. 15A and 15B, in which FIG. 16A is a partial cross-sectional side view illustrating a state at the time of puncture as viewed from the right side, and FIG. 16B is a partial cross-sectional side view illustrating a state at the time of completing insertion of a sensor as viewed from the right side.

FIGS. 19A-19C are views illustrating the biological information detection device of FIG. 17 in a state before puncture, in which FIG. 19A is a partial cross-sectional side view as viewed from the right side, FIG. 19B is a perspective view, and FIG. 19C is a cross-sectional view as viewed from the front side.

FIGS. 20A and 20B are views illustrating the biological information detection device of FIG. 17 in a state immediately after puncture, in which FIG. 20A is a partial cross-sectional side view as viewed from the right side, and FIG. 20B is a partial enlarged view of FIG. 20A.

FIGS. 21A-21C are views illustrating the biological information detection device of FIG. 17 in a state of removing a needle body, in which FIG. 21A is a partial cross-sectional side view illustrating a state immediately after removing the needle body as viewed from the right side, FIG. 21B is a cross-sectional perspective view illustrating a state immediately before removing the needle body, and FIG. 21C is another cross-sectional perspective view illustrating the state immediately before removing the needle body.

FIGS. 22A and 22B are views illustrating the biological information detection device of FIG. 17 in a state at the time of detaching the puncture unit, in which FIG. 22A is a partial cross-sectional side view as viewed from the right side, and FIG. 22B is a perspective view.

DETAILED DESCRIPTION

Hereinafter, a biological information detection device 1 according to a first embodiment of the present disclosure will be illustrated and described in detail with reference to FIGS. 1 to 10.

in the present specification, an up-down direction means an extending direction of a needle body 13a, an upper side is a proximal end side of the needle body 13a (that is, an upward side in FIG. 3), and a lower side is a distal end side of the needle body 13a. In addition, a front side means a direction in which a proximal end portion of a sensor 21 moves (that is, a left side in FIG. 3) when the sensor 21 is inserted into a living body, and a rear side means an opposite direction thereof. Further, a left-right direction means a left-right direction when viewed from the front side toward the rear side.

Figure 1:
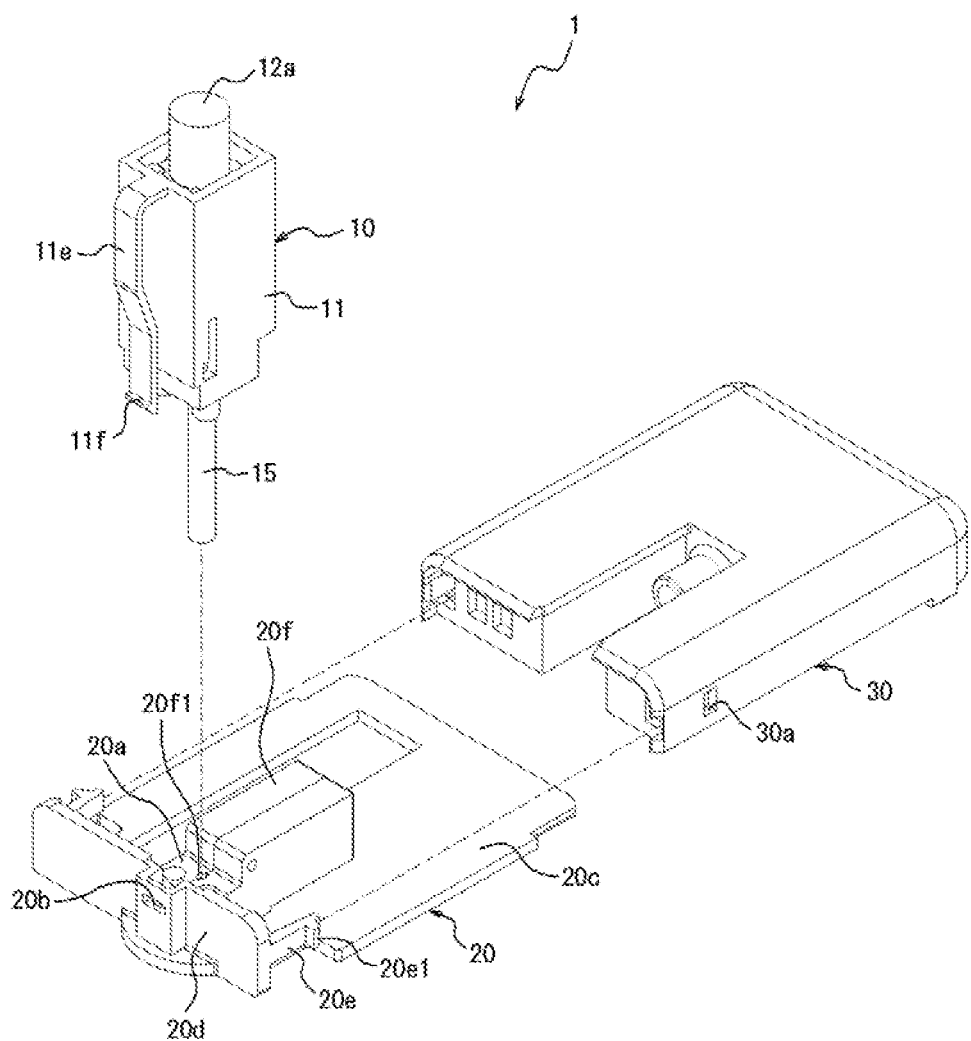
FIG. 1 is an exploded perspective view of a biological information detection device according to a first embodiment of the present disclosure.

As illustrated in FIG. 1, the biological information detection device 1 according to the present embodiment includes a puncture unit 10, a base member 20, and a detector 30. Further, use of the biological information detection device 1 are given schematically as follows. First, the puncture unit 10 is attached to the base member 20, and the detector 30 is attached to a surface of the living body, for example, the skin of a person to be measured, such as a diabetic, in the state of being set on the base member 20 as illustrated in FIG. 2A. Next, when a button 12a of the puncture unit 10 is depressed as illustrated in FIG. 2B, the needle body 13a is shot toward the living body, and puncture is completed. Next, when the detector 30 is advanced with respect to the base member 20, the sensor 21 arranged inside the base member 20 moves and is inserted into the living body (for example, by about several mm below the skin) along the needle body 13a as illustrated in FIG. 2C. Then, the puncture unit 10 is removed from the base member 20 and discarded as illustrated in FIG. 2D, and biological information from the sensor 21, for example, a concentration of an analyte to be detected (for example, glucose, pH, cholesterol, protein, or the like) is detected over a predetermined period (for example, several days) in a state illustrated in FIG. 2E. At the end of the measurement of the biological information, the device illustrated in FIG. 2E is removed from the surface of the living body, and the detector 30 is removed from the base member 20, so that it is possible to reuse the detector 30 together with an unused puncture unit 10 and the base member 20 while discarding the base member 20.

Incidentally, the detected biological information can be transmitted to, for example, a receiver (not illustrated) and displayed in real time on a display unit of the receiver, and the dosage using a medication device provided in the receiver can be automatically adjusted based on the biological information. In addition, the biological information may be stored in a storage device (not illustrated) provided in the detector 30 to be used for a prescription adjust by analyzing the relationship between the dosage and the biological information after the end of a measurement period.

Figure 3:
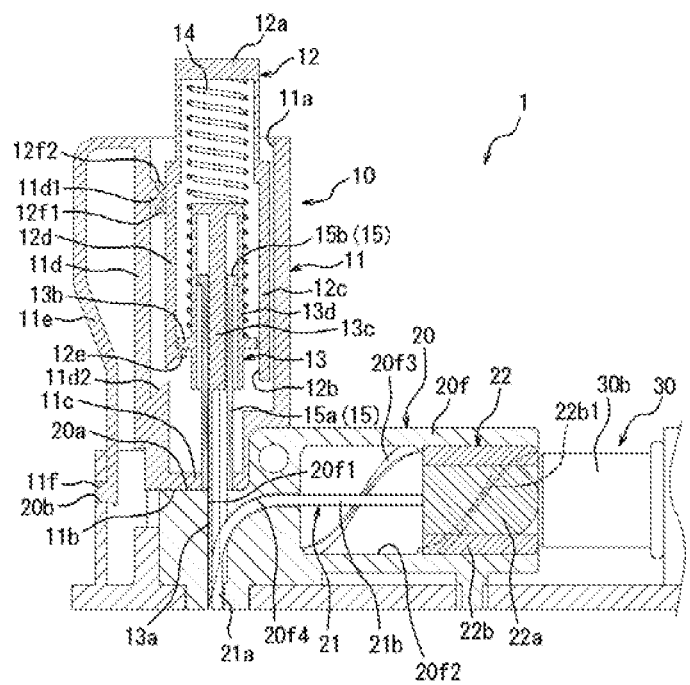
FIG. 3 is a partial cross-sectional side view illustrating the biological information detection device in the state of FIG. 2A as viewed from the right side.

An internal structure of the biological information detection device 1 is given as illustrated in FIG. 3. Incidentally, FIG. 3 is a partial cross-sectional side view illustrating the biological information detection device 1 in the state of FIG. 2A. The puncture unit 10 includes: a housing 11 attachable or detachable to or from the base member 20; a button member 12 arranged to penetrate through an upper opening 11a of the housing 11 and having an upper portion configured as the button 12a; a needle member 13 arranged to penetrate through a lower opening 12b of the button member 12 and having a lower portion configured as the needle body 13a; a biasing member (a coil spring in this embodiment) 14 arranged between the button member 12 and the needle member 13 and biasing the needle member 13 downward; and a cover 15 capable of covering the needle body 13a.

The housing 11 includes a bottom wall 11c forming a fitting convex portion 11b that can be fitted into a fitting concave portion 20a of the base member 20. A through-hole into which the needle body 13a can be inserted is formed in the bottom wall 11c. In addition, an outer peripheral wall 11d having a rectangular shape in a top view with an upper opening 11a formed at an upper end portion is erected at an outer peripheral edge of the bottom wall 11c. A detachment-inhibiting lever 11e, which extends downward and is elastically deformable in the front-rear direction, is provided to be continuous at a front upper end portion of the outer peripheral wall 11d. An engagement protrusion 11f protruding forward is formed at a lower end portion of the detachment-inhibiting lever 11e. When the puncture unit 10 is attached to the base member 20, the engagement protrusion 11f is engaged with an engagement hole 20b, provided in the base member 20, to inhibit the puncture unit 10 from being detached from the base member 20. In addition, when the detachment-inhibiting lever 11e is operated, the engagement with the engagement hole 20b is released, and the puncture unit 10 can be detached.

The button member 12 includes the button 12a having a cylindrical shape with a top at the upper portion thereof. An inner peripheral wall 12c having a rectangular shape in a top view is connected to a lower end portion of the button 12a. The lower opening 12b is formed in a lower end portion of the inner peripheral wall 12c. A slit extending upward from a lower end of the inner peripheral wall 12c is formed between a wall portion on the front side of the inner peripheral wall 12c and a wall portion on the left and right sides, and accordingly, the wall portion on the front side of the inner peripheral wall 12c functions as an elastic arm 12d that is elastically deformable in the front-rear direction. An engagement protrusion 12e capable of locking a flange portion 13b of the needle member 13 is formed on a rear surface of the elastic arm 12d.

In addition, a lower engagement protrusion 12f1 and an upper engagement protrusion 12f2, which can be engaged with an engagement protrusion 11d1 protruding rearward from the upper portion of the opposing outer peripheral wall 11d, are formed on a front upper portion of the wall portion on the front side of the inner peripheral wall 12c. In the state before puncture illustrated in FIG. 3, the needle member 13 is inhibited from coming out upward by the engagement between the engagement protrusion 11d1 and the lower engagement protrusion 12f1. In addition, a protruding portion protruding rearward is provided in a lower portion of the outer peripheral wall 11d opposing the elastic arm 12d, and an upper end surface of the protruding portion forms an inclined surface 11d2 inclined downward toward the front side. A lower end portion of the elastic arm 12d is positioned above a rear side part of the inclined surface 11d2 in the state before puncture illustrated in FIG. 3.

The needle member 13 includes the needle body 13a having a semicircular arc shape in a cross-sectional view of which rear side is cut. A distal end portion of the needle body 13a is sharp and is contained inside the base member 20 in the state before puncture illustrated in FIG. 3. A shaft 13c having a columnar shape is connected to a proximal end portion of the needle body 13a. A tube wall 13d is provided on an outer peripheral side of the shaft 13c with an annular gap interposed therebetween, and an upper end portion of the shaft 13c and an upper end portion of the tube wall 13d are connected by a disk-shaped top wall. The flange portion 13b is formed on an outer peripheral surface of the tube wall 13d. The biasing member 14 is arranged between an upper surface of the flange portion 13b and a lower surface of the button 12a. In the state before insertion illustrated in FIG. 3, the engagement protrusion 12e of the elastic arm 12d locks the flange portion 13b to hold a biasing force of the biasing member 14 that biases the needle body 13a downward.

The cover 15 is arranged in the annular gap formed on the outer peripheral side of the shaft 13c so as to be vertically slidable. The cover 15 includes a cylindrical tube portion 15a and an engagement protrusion 15b that has an annular shape and is formed on an outer peripheral surface of an upper end of the tube portion 15a. The tube portion 15a can pass through the through-hole formed in the bottom wall 11c of the housing 11, but the engagement protrusion 15b is not allowed to pass through the through-hole. Therefore, the cover 15 protrudes from the housing 11 by its own weight to cover and hide the needle body 13a in a state in which the puncture unit 10 is detached from the base member 20 as illustrated in FIG. 1 and FIG. 2D.

As illustrated in FIG. 1, the base member 20 includes a substantially rectangular bottom plate 20c having a bottom surface that can be affixed to the surface of the living body. A substantially rectangular vertical wall 20d is erected on a front end edge of the bottom plate 20c. The vertical wall 20d is provided with the engagement hole 20b that is engaged with the engagement protrusion 11f of the detachment-inhibiting lever 11e of the puncture unit 10 described above. In addition, a pair of engagement pieces 20e are provided at both left and right end portions of the vertical wall 20d. Each of the pair of engagement pieces 20e has an engagement protrusion 20e1, and these engagement protrusions 20e1 are locked with the engagement hole 30a of the detector 30 when the detector 30 is advanced as illustrated in FIG. 2C. In addition, at the end of the measurement of the biological information, the engagement piece 20e of the detector 30 is elastically deformed to release the engagement between the engagement protrusion 20e1 and the engagement hole 30a, and the detector 30 can be removed from the base member 20.

A substantially rectangular parallelepiped (cuboid) base 20f is provided at the rear of the engagement hole 20b of the vertical wall 20d. The fitting concave portion 20a for fitting the above-described puncture unit 10 is provided at a front part of an upper surface of the base 20f. A straight through-hole 20f1 extending in the up-down direction through which the needle body 13a can penetrate is formed in the fitting concave portion 20a. It is configured such that an upper surface side of the inside of the through-hole 20f1 is sealed with rubber or the like in order to prevent infection.

As illustrated in FIG. 3, the sensor 21 having an elongated shape and an end member 22 fixed to the proximal end portion of the sensor 21 are arranged inside the base 20f. The sensor 21 includes a measurement light emitting portion 21a arranged at the distal end portion of the sensor 21 and a light guide portion 21b that is connected to the proximal end portion of the measurement light emitting portion 21a and extends to the proximal end portion of the sensor 21. The light guide portion 21b has an optical fiber and can transmit excitation light incident from the proximal end portion of the sensor 21 to the measurement light emitting portion 21a and transmit measurement light generated in the measurement light emitting portion 21a by the excitation light to the proximal end portion of the sensor 21. The measurement light emitting portion 21a includes a fluorescent gel containing a fluorescent label (dye) fluorescing with the excitation light, and this fluorescence gel generates the fluorescence (measurement light) corresponding to concentration of the analyte to be monitored.

The end member 22 includes a collimating lens 22a as a light adjustment portion. The collimating lens 22a collects the measurement light diffused from the proximal end portion of the sensor 21 so as to become collimated light. In addition, the collimating lens 22a can collect the excitation light incident from the detector 30 and transmit the collected light to the proximal end portion of the sensor 21. Incidentally, an inner tube 22b that holds the collimating lens 22a is provided on an outer peripheral side of the substantially columnar collimating lens 22a. The inner tube 22b has a cylindrical outer peripheral surface.

An end member guide path 20f2 that guides the end member 22 is provided on the base 20f. The end member guide path 20f2 has a cylindrical inner peripheral surface and extends in the front-rear direction. In addition, the inner peripheral surface of the end member guide path 20f2 and the outer peripheral surface of the inner tube 22b are connected via a screw portion. In this example, the screw portion is configured using a screw groove 22b1 formed on the outer peripheral surface of the inner tube 22b and a screw thread 20f3 formed on the inner peripheral surface of the end member guide path 20f2, and causes the end member 22 to rotate in accordance with the forward movement of the end member 22.

A sensor guide path 20f4 that guides the sensor 21 is provided in front of the end member guide path 20f2. The sensor guide path 20f4 has a cylindrical inner peripheral surface and a proximal end portion positioned on an axis center of the end member guide path 20f2. In addition, the sensor guide path 20f4 is gradually curved from the proximal end portion thereof downward as approaching the through-hole 20f1 where the needle body 13a is arranged, and is connected to the through-hole 20f1. In the state before puncture illustrated in FIG. 3, the distal end portion of the sensor 21 is contained in the through-hole 20f1, and the end member 22 is arranged at a rear end of the end member guide path 20f2. The rear side of the end member guide path 20f2 is open so that the cylindrical insertion tube portion 30b of the detector 30 can be inserted from this open portion.

The detector 30 includes a light emitting portion (not illustrated) that generates the excitation light to be incident on the end member 22 through the insertion tube portion 30b. In addition, the detector 30 includes a light receiving portion (not illustrated) that receives the measurement light incident from the end member 22 through the insertion tube portion 30b. In addition, the detector 30 includes a detection unit (not illustrated) that detects the concentration of the analyte to be detected based on the measurement light received by the light receiving portion.

Figure 4:
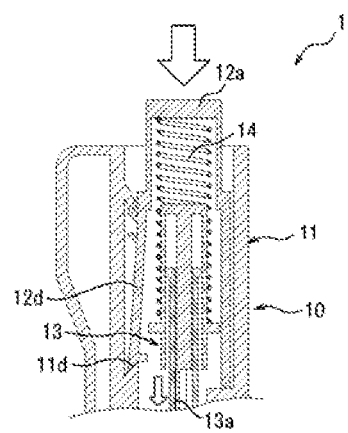
FIG. 4 is a cross-sectional view illustrating the biological information detection device in the state of FIG. 2B as viewed from the right side.

Instructions to form the state before puncture illustrated in FIG. 2A to the state after insertion of the sensor 21 illustrated in FIG. 2C in the biological information detection device 1 are given as follows. First, when the button 12a is depressed as illustrated in FIG. 4, the lower end portion of the elastic arm 12d abuts and slides on the inclined surface 11d2 of the housing 11, and the elastic arm 12d is elastically deformed forward. As a result, the engagement between the elastic arm 12d and the needle member 13 is released, and the needle body 13a is shot toward the living body by the biasing force of the biasing member 14.

Figure 5:
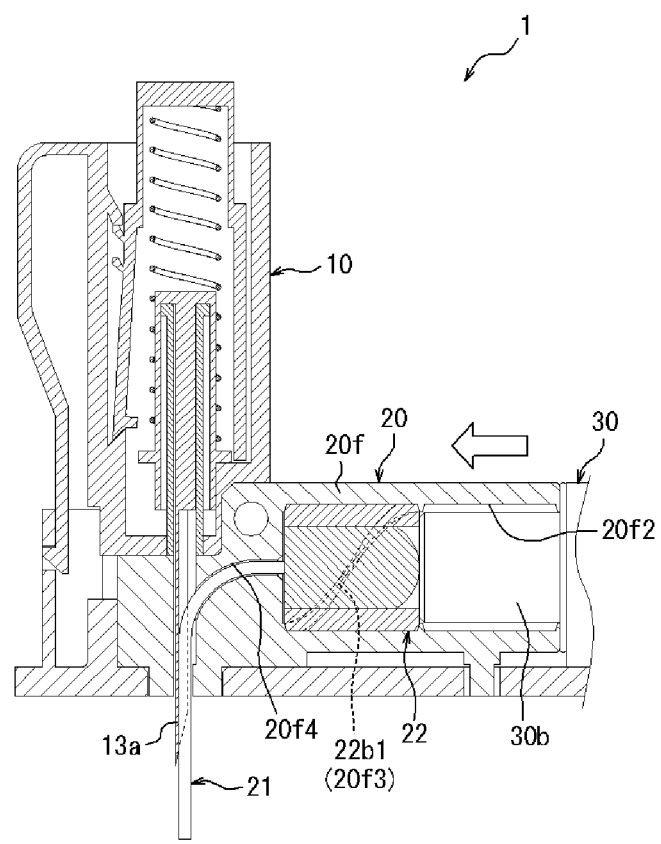
FIG. 5 is a partial cross-sectional side view illustrating the biological information detection device in the state of FIG. 2C as viewed from the right side.
Figure 6:
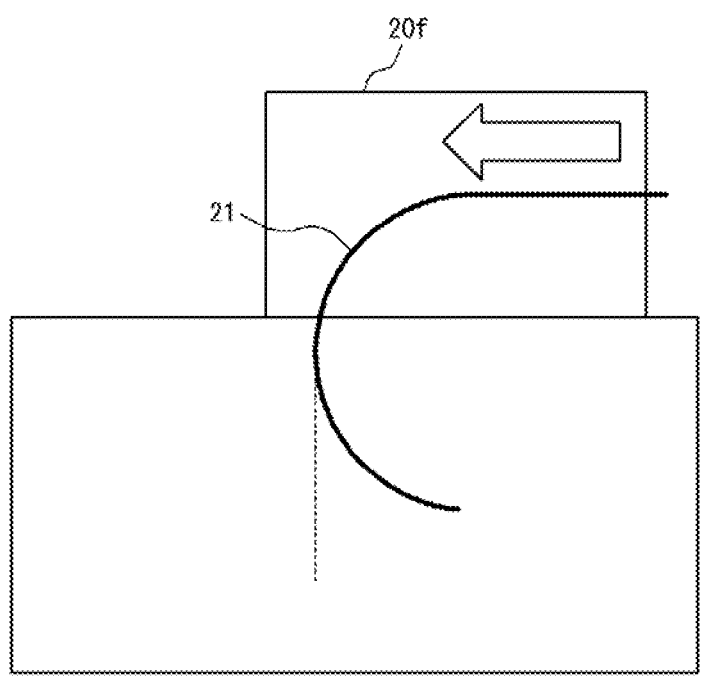
FIG. 6 is a cross-sectional view schematically illustrating an arrival position of a sensor in a case where a sensor is inserted into a living body with a bending tendency as viewed from the right side.

When the detector 30 is advanced as illustrated in FIG. 5 in the state where the distal end portion of the needle body 13a has pierced the living body, the insertion tube portion 30b of the detector 30 is inserted into the end member guide path 20f2. At this time, the rear end surface of the end member 22 is pushed by the front end surface of the insertion tube portion 30b, and thus, the end member 22 advances while rotating by the screw portion (the screw groove 22b1 and the screw thread 20f3). In addition, since the sensor 21 is fixed to the end member 22, the sensor 21 also moves while rotating, and the distal end portion thereof is guided by the inner surface of the needle body 13a and is inserted into the living body.

Here, a reason why the sensor 21 is inserted into the living body while being rotated is given as follows. When a radius of curvature of the sensor guide path 20f4 is set to be small in order to reduce a height of the device from the surface of the living body at the time of measurement, there is concern that the sensor 21 may easily tend to be bent. When the sensor 21 is inserted into the living body in the state of having the bending tendency, there is a risk that sensor 21 is not inserted straight as indicated by the solid line in FIG. 6, and the distal end portion of the sensor 21 does not reach a desired depth. Thus, in this example, even if the sensor 21 has the bending tendency, the influence of the bending tendency is dispersed around the entire circumference by inserting the sensor 21 into the living body while rotating, so that the distal end portion of the sensor 21 is can be inserted linearly.

Figure 7A:
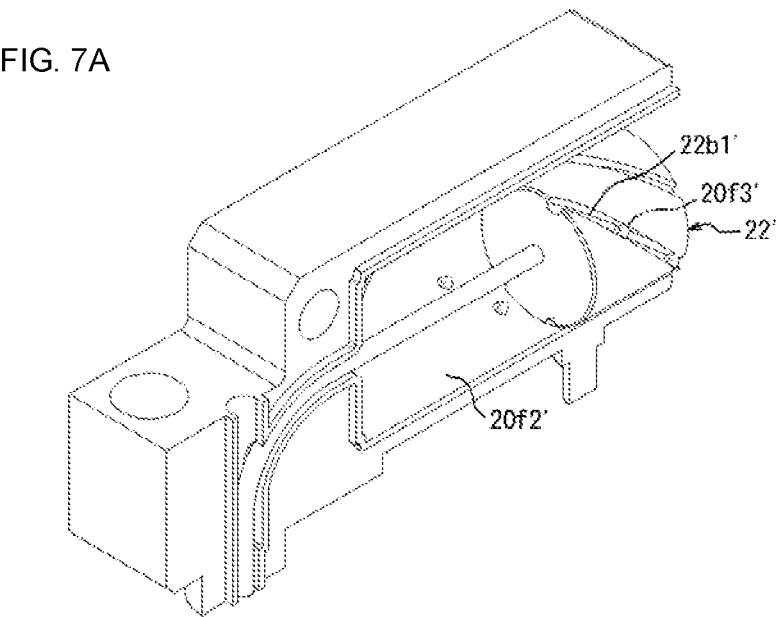
Figure 7B:
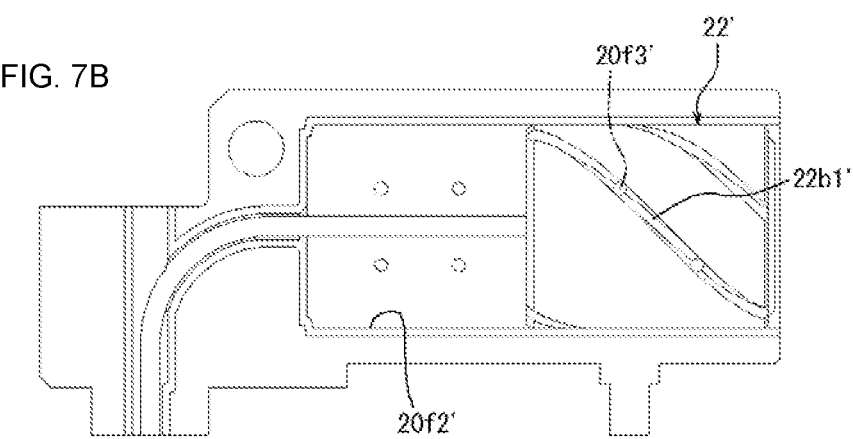
Figure 8:
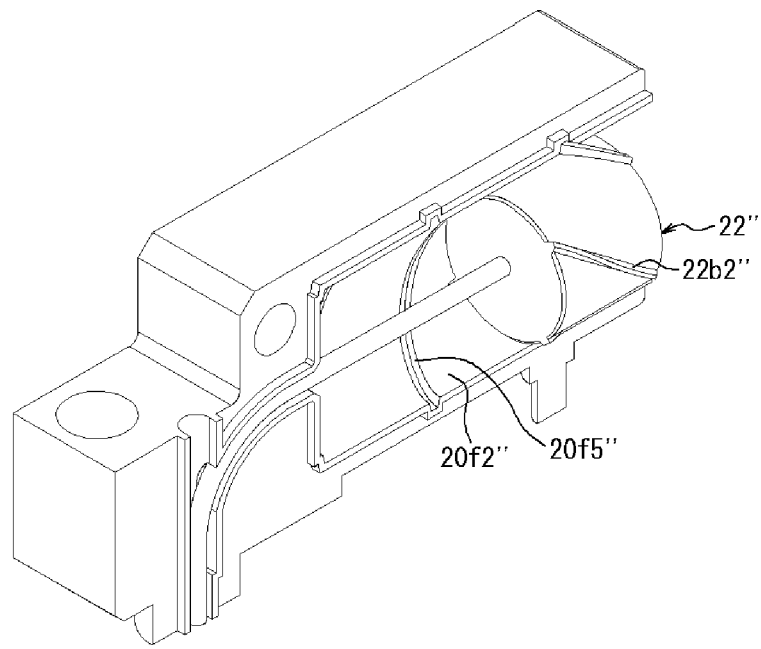
FIG. 8 is a perspective view illustrating another modified example of the biological information detection device of FIG. 1.

In this manner, the screw portion configured to rotate the sensor 21 can also adopt a configuration illustrated in FIG. 7 as a modified example. That is, in the present modified example, an end member guide path 20f2' has a plurality of protrusions 20f3' that can be engaged with a screw groove 22b1' of an end member 22'. With such a configuration, it is possible to reduce sliding resistance of the screw portion and to enable smoother movement and rotation of the end member 22'. In addition, it is also possible to adopt a configuration illustrated in FIG. 8 as another modified example. In the present modified example, an end member guide path 20f2" has a screw groove 20f5", and an end member 22" has a screw thread 22b2". Incidentally, inclination angles of the screw threads 20f3 and 22b2" of the screw portions, the protrusions 20f3', and the screw grooves 22b1, 22b1', and 20f5" with respect to the axial direction is preferably 45° or smaller because of the smooth movement and rotation of the end members 22, 22', and 22".

As described above, the biological information detection device 1 according to the present embodiment includes: the sensor 21 that has the elongated shape and enables detection of the biological information by causing the distal end portion to indwell inside the living body; and the needle body 13a that pierces the living body to insert the distal end portion of the sensor 21 into the living body, and is configured such that the distal end portion of the sensor 21 can be inserted into the living body along the needle body 13a piercing in the living body.

Therefore, with the biological information detection device 1 according to the present embodiment, the sensor 21 can be inserted into the living body separately from the needle body 13a, and thus, the distal end portion of the sensor 21 can indwell at a desired depth in the living body.

In addition, the biological information detection device 1 according to the present embodiment is configured such that the proximal end portion of the sensor 21 is movable in the direction different from the extending direction of the needle body 13a.

Therefore, with the biological information detection device 1 according to the present embodiment, the sensor 21 can be pushed from the direction different from the extending direction of the needle body 13a, and it is possible to achieve the simple configuration by separating a mechanism for pushing (inserting) the needle body 13a and a mechanism for pushing (inserting) the sensor 21.

In addition, the biological information detection device 1 according to the present embodiment is configured such that the proximal end portion of the sensor 21 is movable in the direction along the surface of the living body.

Therefore, with the biological information detection device 1 according to the present embodiment, it is possible to push and insert the sensor 21 from the direction along the surface of the living body, and to suppress the height of the mechanism for pushing and inserting the sensor 21 with respect to the surface of the living body. Thus, it is possible to improve an attachment feeling by making it hard to get caught by clothing when the biological information detection device 1 is attached to the surface of the living body.

In addition, the biological information detection device 1 according to the present embodiment is configured such that the sensor 21 includes the measurement light emitting portion 21a that is arranged at the distal end portion of the sensor 21 and generating light, and the light guide portion 21b that transmits the light from the measurement light emitting portion 21a to the proximal end portion of the sensor 21.

Therefore, with the biological information detection device 1 according to the present embodiment, it is possible to improve the measurement accuracy and extend life of the sensor 21 by using the sensor 21 of an optical type.

In addition, the biological information detection device 1 according to the present embodiment includes the end member 22 that is fixed to the proximal end portion of the sensor 21 and allows at least light from the proximal end portion of the sensor 21 to pass therethrough, and is configured such that the end member 22 includes the light adjustment portion (the collimating lens 226a) that collects the light diffused from the proximal end portion of the sensor 21.

Therefore, with the biological information detection device 1 according to the present embodiment, it is possible to mitigate the accuracy requirement for a distance in an optical axis direction between the light receiving portion of the detector 30 and the end member 22.

In addition, the biological information detection device 1 according to the present embodiment is configured such that the light adjustment portion (the collimating lens 226a) collects the light diffused from the proximal end portion of the sensor 21 so as to become the collimated light.

Therefore, with the biological information detection device 1 according to the present embodiment, it is possible to minimize the accuracy requirement for a distance in an optical axis direction between the light receiving portion of the detector 30 and the end member 22.

In addition, the biological information detection device 1 according to the present embodiment includes: the end member 22 that is fixed to the proximal end portion of the sensor 21 and allows at least the signal (measurement light) corresponding to the concentration of the analyte to be detected obtained from the sensor 21 to pass therethrough; the base member 20 that is affixable to the surface of the living body; the end member guide path 20f2 that is provided in the base member 20 and guides the end member 22; and the detector 30 that has the reception unit (light receiving portion) receiving the signal from the end member 22 and the detection unit detecting the concentration of the analyte to be monitored based on the signal received by the reception unit, and is configured such that the detector 30 is attachable or detachable to or from the base member 20.

Therefore, with the biological information detection device 1 according to the present embodiment, it is possible to reuse the detector 30.

In addition, the biological information detection device 1 according to the present embodiment is configured such that the distal end portion of the sensor 21 is inserted into the living body along the needle body 13a by pushing and moving the end member 22 by the detector 30.

Therefore, with the biological information detection device 1 according to the present embodiment, it is possible to insert the sensor 21 by moving the detector 30, and to ensure the transmission of the signal to the detector 30 after the insertion of the sensor 21. In particular, when the sensor 21 is of the optical type as in the present embodiment, it is possible to enhance the accuracy of the distance in the optical axis direction between the light receiving portion of the detector 30 and the end member 22 at the time of completing the insertion of the sensor 21, and to enhance the detection accuracy of the biological information.

In addition, the biological information detection device 1 according to the present embodiment is configured such that, as the end member 22 is pushed and moved by the detector 30, the end member 22 rotates in accordance with the movement.

Therefore, with the biological information detection device 1 according to the present embodiment, it is possible to reduce the influence of the bending tendency of the sensor 21, to more linearly insert the sensor 21 into the living body, and to reliably insert the distal end portion of the sensor 21 to a desired depth in the living body, and, the measurement with higher accuracy can be realized.

In addition, the biological information detection device 1 according to the present embodiment is configured such that the end member guide path 20f2 has the cylindrical inner peripheral surface to accommodate the end member 22, and the inner peripheral surface of the end member guide path 20f2 and the outer peripheral surface of the end member 22 are connected via the screw portion (the screw groove 22b1, the screw thread 20f3, the screw groove 22b1', the plurality of protrusions 20f3', the screw groove 20f5', and the screw thread 22b2") that rotates the end member 22 in accordance with the movement of the end member 22.

Therefore, with the biological information detection device 1 according to the present embodiment, the sensor 21 can be rotated in conjunction with the pushing operation of the detector 30, and thus, it is possible to make the operation for inserting the sensor 21 while rotating the sensor 21 easy.

In addition, it is configured in the above-described embodiment such that the sensor 21 is rotated in conjunction with the pushing operation of the detector 30 as a countermeasure against the bending tendency of the sensor 21. Instead of such a configuration, however, it may be configured such that a rotation operation may be added at the time of inserting the detector 30A as illustrated in FIG. 9.

Figure 9:
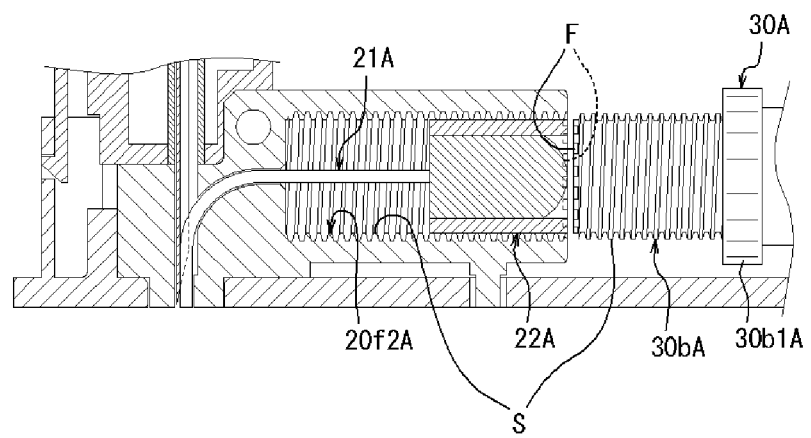
FIG. 9 is a partial cross-sectional side view illustrating still another modified example of the biological information detection device of FIG. 1 as viewed from the right side.

In a modified example illustrated in FIG. 9, an end member guide path 20f2A has a cylindrical inner peripheral surface that accommodates the end member 22, the end member 22A has a cylindrical outer peripheral surface, and a detector 30A includes an insertion tube portion 30bA having a cylindrical outer peripheral surface that can be inserted into the end member guide path 20f2A and an operation portion 30b1A rotatable integrally with the insertion tube portion 30bA. In addition, the inner peripheral surface of the end member guide path 20f2A and the outer peripheral surface of the insertion tube portion 30bA can be connected via a screw portion S that moves the insertion tube portion 30bA toward the depth of the end member guide path 20f2A in accordance with a rotation operation of the operation portion 30b1A. Further, a distal end surface of the insertion tube portion 30bA and a proximal end surface of the end member 22A can be connected via a fitting portion F that inhibits mutual rotation.

Figure 10:
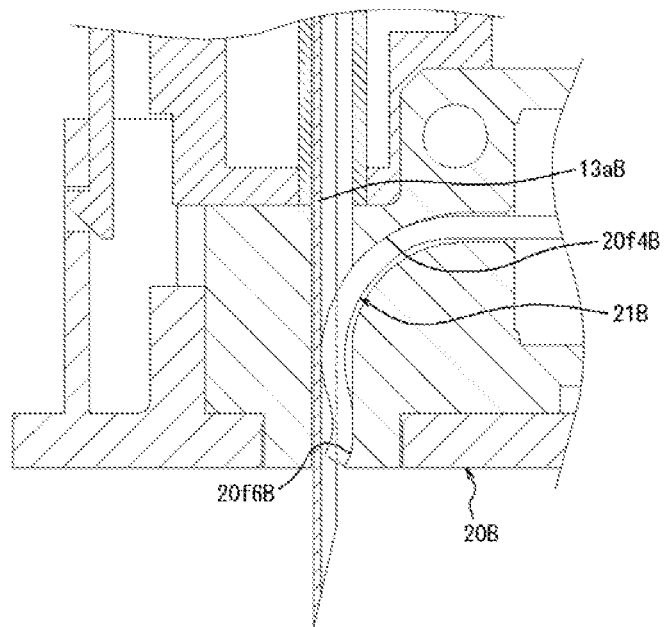
FIG. 10 is a partial cross-sectional side view illustrating still another modified example of the biological information detection device of FIG. 1 as viewed from the right side.
Figure 11A:
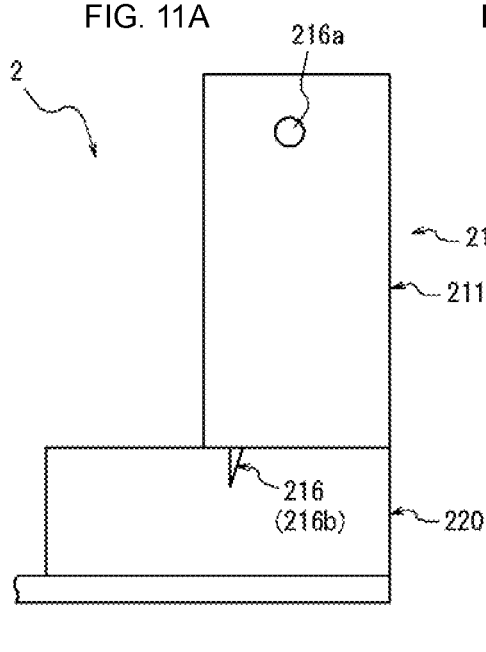
Figure 11B:
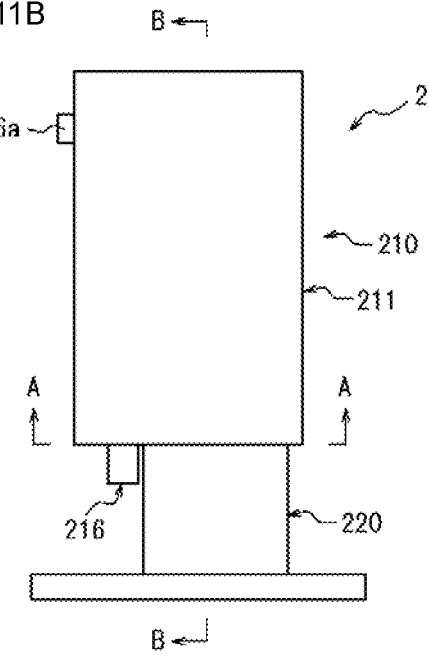
Figure 11C:
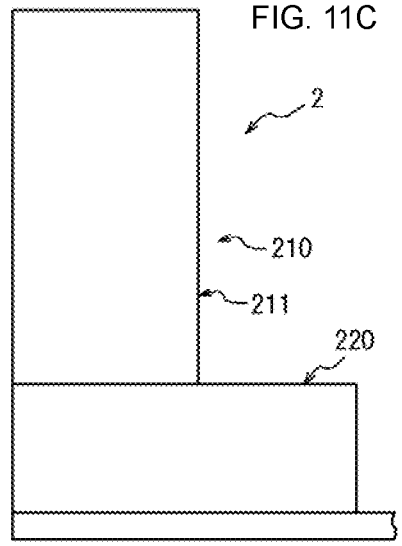
Figure 11D:
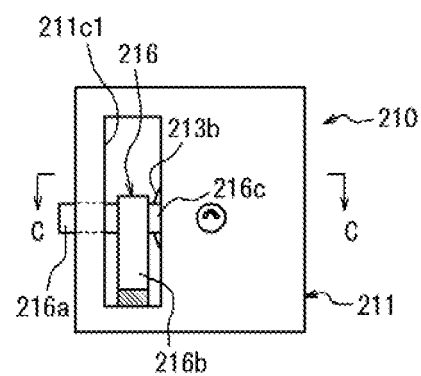
Figure 12A:
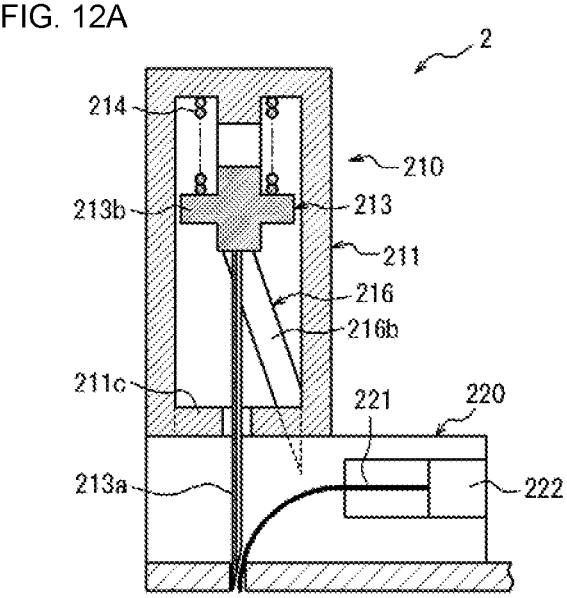
FIG. 12A is a cross-sectional view taken along a line B-B of FIG. 11B.
Figure 12B:
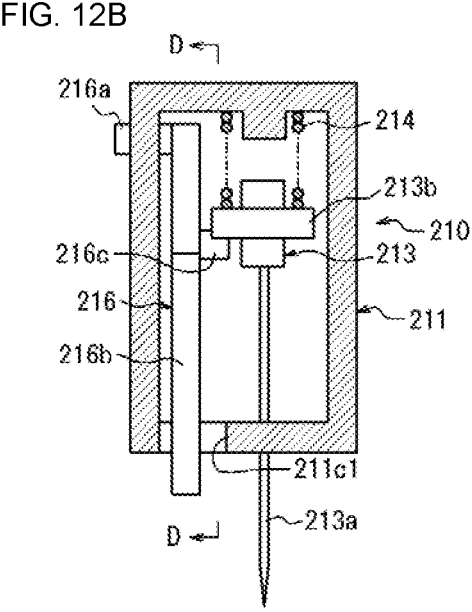
FIG. 12B is a cross-sectional view taken along a line C-C of FIG. 11D.
Figure 12C:
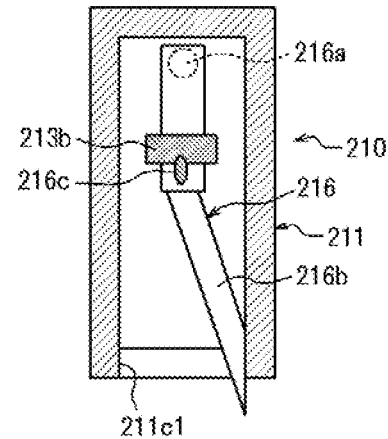
FIG. 12C is a cross-sectional view taken along a line D-D of FIG. 12B.

Further, as a countermeasure against such a bending tendency, it may be configured such that the bending tendency is corrected by bending a guide path in a reverse direction on an outlet side as illustrated in FIG. 10, instead of rotating the sensor 21A. In a modified example illustrated in FIG. 10, a base member 20B is provided with a sensor guide path 20f4B that guides a sensor 21B, the sensor guide path 20f4B is gradually curved downward as approaching a needle body 13aB, and a reversely curved guide portion 20f6B, which guides the sensor 21B to be curved in a direction opposite from a curved direction of the sensor guide path 20f4B, is provided in the sensor guide path 20f4B on a side close to the needle body 13aB. According to such a configuration, it is unnecessary to provide a screw portion configured to rotate the sensor 21B, and thus, it is possible to make a structure simple.

Next, a biological information detection device 2 according to a second embodiment of the present disclosure will be illustrated and described in detail with reference to FIGS. 11A, 11B, 11C, 11D, 12A, 12B, 12C, 13A, and 13B.

The biological information detection device 2 according to the present embodiment has a different configuration from the case of the embodiment that has been described with reference to FIGS. 1 to 10 in terms that a needle body 213a pierces a living body by moving a detector 230 with respect to a base member 220, and has the same configuration other than this point.

Specifically, in the present embodiment, an puncture unit 210 includes a housing 211, a puncturing needle holding member 213, a puncturing biasing member (a coil spring in this example) 214, and a lever member 216 as a puncturing movable portion as illustrated in FIGS. 11 and 12. The housing 211 has a hollow rectangular parallelepiped shape, and is provided with a through-hole, which allows the needle body 213a held by the puncturing needle holding member 213 to penetrate therethrough, in a bottom wall 211c thereof. In addition, a left wall of the housing 211 is provided with a through-hole that holds a swing shaft 216a of the lever member 216 so as to be swingable, and the bottom wall 211c of the housing 211 is provided with a slot 211c1 that allows a lower end portion of the lever member 216 to penetrate therethrough.

The lever member 216 is provided with a lever main body 216b having a polygonal line shape in which a part from a middle portion to a lower end portion in the up-down direction is bent rearward at the middle portion in the up-down direction, and the swing shaft 216a is provided protrude on the left wall in an upper portion of the lever main body 216b. In addition, an engagement protrusion 216c that can be engaged with a flange portion 213b provided in an upper portion of the puncturing needle holding member 213 is provided to protrude on a right wall at the middle portion of the lever main body 216b in the up-down direction. The puncturing biasing member 214 is arranged between a ceiling wall of the housing 211 and the flange portion 213b. In a state before puncture illustrated in FIGS. 11 and 12, the engagement protrusion 216c of the lever member 216 locks the flange portion 213b of the puncturing needle holding member 213 in a state in which the puncturing needle holding member 213 receives a biasing force from the puncturing biasing member 214.

Figure 13A:
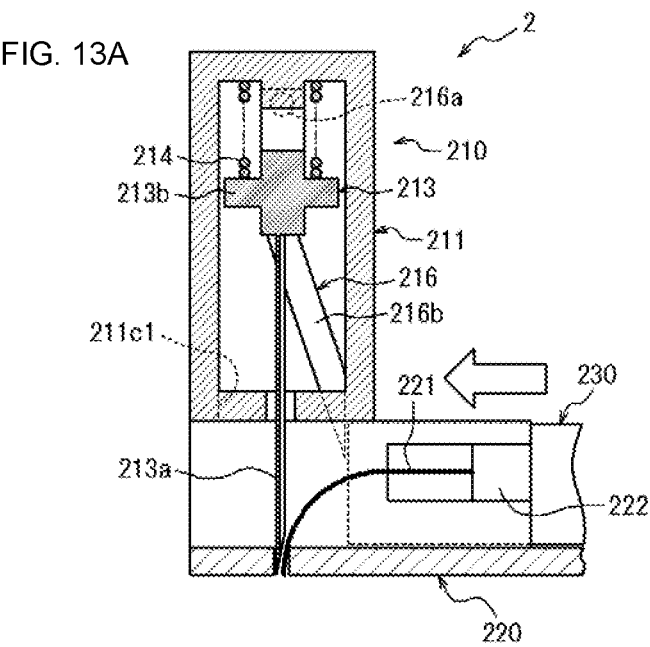
Figure 13B:
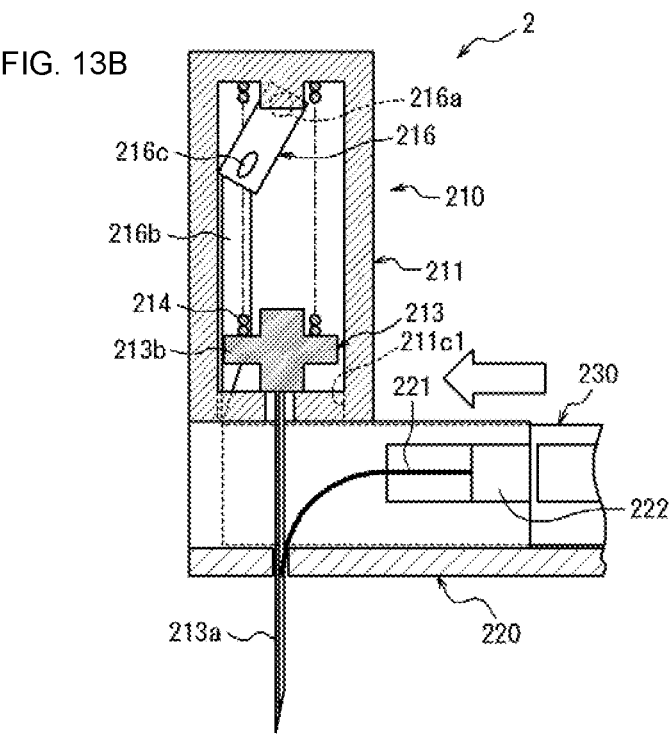

When the detector 230 is moved with respect to the base member 220 as illustrated in FIG. 13A from the above-described state, the lower end portion of the lever member 216 is pushed by the detector 230 and moves forward inside the slot 211c1. The lever member 216 swings about the swing shaft 216a in accordance with the movement of the lower end portion of the lever member 216, and the engagement between the lever member 216 and the puncturing needle holding member 213 is released. Therefore, the puncturing needle holding member 213 is depressed by the biasing force from the puncturing biasing member 214 as illustrated in FIG. 13B, and the needle body 213a pierces the living body.

In this manner, the biological information detection device 2 according to the present embodiment is configured such that the needle body 213a pierces the living body by moving the detector 230 with respect to the base member 220, and an end member 222 is pushed and moved by further moving the detector 230 so that the distal end portion of the sensor 221 is inserted into the living body along the needle body 213a.

Therefore, with the biological information detection device 2 according to the present embodiment, it is possible to realize the puncture of the needle body 213a and the insertion of the sensor 221 through a series of operations of moving the detector 230, and thus, it is possible to make the operation easy.

In addition, the biological information detection device 2 according to the present embodiment includes: the puncturing needle holding member 213 that holds the needle body 213a; the puncturing biasing member 214 that biases the puncturing needle holding member 213 toward the surface of the living body; and the puncturing movable portion (the lever member 216) that is engaged with the puncturing needle holding member 213 to hold the state in which the puncturing needle holding member 213 receives the biasing force from the puncturing biasing member 214, and is configured such that the puncturing movable portion (the lever member 216) is released from engagement with the puncturing needle holding member 213 by being pushed by the detector 230 as the detector 230 is moved with respect to the base member 220.

Therefore, with the biological information detection device 2 according to the present embodiment, it is possible to realize the easy operation with the simple configuration.

Next, a biological information detection device 3 according to a third embodiment of the present disclosure will be illustrated and described in detail with reference to FIG. 14.

The biological information detection device 3 according to the present embodiment has a different configuration from the case of the embodiment that has been described with reference to FIGS. 1 to 10 in terms that a puncture unit 310 is detachable from a base member 320 by moving a detector 330 with respect to the base member 320, and has the same configuration other than this point.

Specifically, in the present embodiment, the puncture unit 310 includes a detachment-inhibiting lever 311e as a detachment-inhibiting movable portion as illustrated in FIG. 14A. As illustrated in FIG. 14B, the detachment-inhibiting lever 311e is configured to be locked by a vertical wall 320d of the base member 320 from the front side. That is, an engagement protrusion 311f protruding rearward is formed at a lower end portion of the detachment-inhibiting lever 311e. When the puncture unit 310 is attached to the base member 320, the engagement protrusion 311f is engaged with an engagement hole 320b, provided in the vertical wall 320d, to inhibit the puncture unit 310 from being detached from the base member 320.

In addition, a pair of extension portions 311e1 protruding in the left-right direction are provided at the lower end portion of the detachment-inhibiting lever 311e. As illustrated in FIG. 14C, the pair of extension portions 311e1 are pushed forward by the detector 330 so as to release the engagement between the detachment-inhibiting lever 311e and the base member 320 when the detector 330 is moved with respect to the base member 320, and the insertion of the distal end portion of a sensor 321 into the living body is completed.

As described above, the biological information detection device 3 according to the present embodiment includes the puncture unit 310 that holds the needle body 313a and is detachable from the base member 320, and moves the detector 330 with respect to the base member 320, and is configured such that the puncture unit 310 is detachable from the base member 320 when the detector 330 is moved with respect to the base member 320 and the insertion of the distal end portion of the sensor 321 into the living body is completed.

Therefore, with the biological information detection device 3 according to the present embodiment, it is possible to realize the insertion of the sensor 321 and enabling of enabling detachment of the puncture unit 310 through a series of operations of moving the detector 330, and thus, it is possible to make the operation easy.

In addition, the biological information detection device 3 according to the present embodiment is configured such that the puncture unit 310 has the detachment-inhibiting movable portion (the detachment-inhibiting lever 311e) that is engaged with the base member 320 to inhibit detachment of the puncture unit 310 from the base member 320, and the detachment-inhibiting movable portion (the detachment-inhibiting inhibiting lever 311e) is released from engagement with the base member 320 by being pushed by the detector 330 when insertion of the distal end portion of the sensor 321 into the living body is completed.

Therefore, with the biological information detection device 3 according to the present embodiment, it is possible to realize the easy operation with the simple configuration.

Incidentally, the configuration of the detachment-inhibiting movable portion (the detachment-inhibiting lever 311e) of the present embodiment can also be applied to the second embodiment that has been described with reference to FIGS. 11A, 11B, 11C, 11D, 12A, 12B, 12C, 13A, and 13B.

Next, a biological information detection device 4 according to a fourth embodiment of the present disclosure will be illustrated and described in detail with reference to FIGS. 15A, 15B, 16A, and 16B.

The biological information detection device 4 according to the present embodiment has a different configuration from the case of the embodiment that has been described with reference to FIGS. 1 to 10 in terms that a needle body 413a is removed from a living body by moving a detector 430 with respect to a base member 420, and has the same configuration other than this point.

Figure 15A:
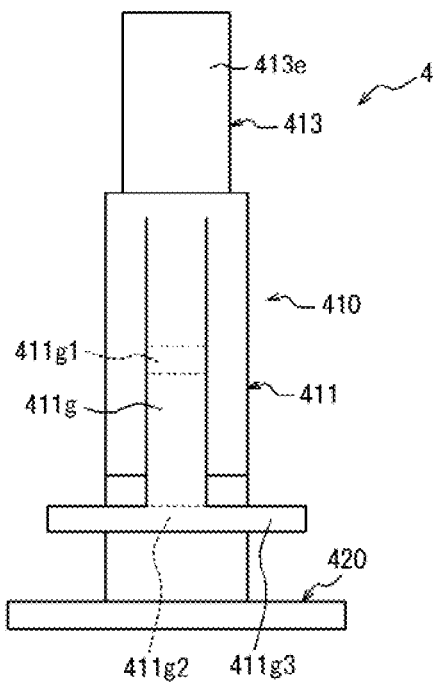
Figure 15B:
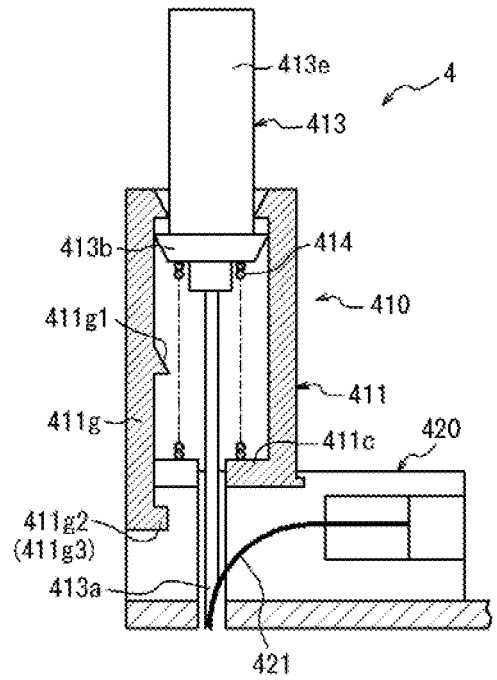

Specifically, in the present embodiment, the puncture unit 410 includes a removing needle holding member 413, a housing 411, and a removing biasing member (a coil spring in this example) 414 as illustrated in FIGS. 15A and 15B. The removing needle holding member 413 includes: the needle body 413a; a flange portion 413b having a rectangular shape in a plan view to be continuous to a proximal end portion of the needle body 413a; and a columnar depressing operation portion 413e continuous to a proximal end portion of the flange portion 413b. The housing 411 has a hollow rectangular parallelepiped shape, and is provided with a through-hole, which allows the needle body 413a held by the removing needle holding member 413 to penetrate therethrough, in a bottom wall 411c thereof. In addition, a ceiling wall of the housing 411 is provided with a through-hole that allows the depressing operation portion 413e of the removing needle holding member 413 to penetrate therethrough while inhibiting upward withdrawal.

Further, a lever body 411g as a removing movable portion is formed on a side wall on the front side of the housing 411. An engagement protrusion 411g1 capable of locking the flange portion 413b of the removing needle holding member 413 is provided to protrude on a rear surface of a middle portion in the up-down direction of the lever body 411g. In addition, an engagement protrusion 411g2 for inhibiting detachment, which is locked by the base member 420 to inhibit detachment of the puncture unit 410 from the base member 420, is provided to protrude on a rear surface of a lower end portion of the lever body 411g. Further, a pair of extension portions 411g3 protruding in the left-right direction are provided on the lower end portion of the lever body 411g. In addition, the removing biasing member 414 is arranged between the bottom wall 411c of the housing 211 and the flange portion 213b.

Therefore, with the biological information detection device 4 according to the present embodiment, the needle body 413a can first pierce the living body by depressing the depressing operation portion 413e of the removing needle holding member 413 as illustrated in FIG. 16A. Then, when such a puncture state is formed, the flange portion 413b of the removing needle holding member 413 is locked by the engagement protrusion 411g1 of the lever body 411g, thereby holding an upward biasing force of the removing biasing member 414 with respect to the removing needle holding member 413.

In this state, if the detector 430 is advanced, the sensor 421 can be inserted into the living body. Then, at the time of completing the insertion, the pair of extension portions 411g3 of the lever body 411g are pushed by the detector 430, and the lever body 411g swings forward. The engagement between the engagement protrusion 411g1 of the lever body 411g and the flange portion 413b of the removing needle holding member 413 is released due to the swing of the lever body 411g, the removing needle holding member 413 moves upward by the biasing force of the removing biasing member 414, and the needle body 413a is removed from the living body. In addition, the engagement between the engagement protrusion 411g2 of the lever body 411g and the base member 420 is also released due to the swing of the lever body 411g, and thus, the puncture unit 410 can be detached from the base member 420.

As described above, the biological information detection device 4 according to the present embodiment is configured such that the needle body 413a is removed from the living body when the detector 430 is moved with respect to the base member 420 and the insertion of the distal end portion of the sensor 421 into the living body is completed.

Therefore, with the biological information detection device 4 according to the present embodiment, it is possible to realize both the insertion of the sensor 421 and the removal of the needle body 413a through a series of operations of moving the detector 430, and thus, it is possible to make the operation easy.

In addition, the biological information detection device 4 according to the present embodiment includes: the removing needle holding member 413 that holds the needle body 413a; the removing biasing member 414 that biases the removing needle holding member 413 in the direction to be removed from the living body; and the removing movable portion (the lever body 411g) that is engaged with the removing needle holding member 413 to hold the state in which the removing needle holding member 413 receives the biasing force from the removing biasing member 414, and is configured such that the removing movable portion (the lever body 411g) is released from engagement with the removing needle holding member 413 by being pushed by the detector 430 when insertion of the distal end portion of the sensor 421 into the living body is completed.

Therefore, with the biological information detection device 4 according to the present embodiment, it is possible to realize the easy operation with the simple configuration.

Next, a biological information detection device 5 according to a fifth embodiment of the present disclosure will be illustrated and described in detail with reference to FIGS. 17, 18, 19A, 19B, 19C, 20A, 20B, 21A, 21B, 21C, 22A, and 22B.

The biological information detection device 5 according to the present embodiment has a different configuration from the case of the embodiment that has been described with reference to FIGS. 1 to 10 in terms that puncture of a needle body 513a, removal of the needle body 513a, and enabling detachment of a puncture unit 510 are realized by moving a detector 530 with respect to a base member 520, and has the same configuration other than this point.

Figure 17:
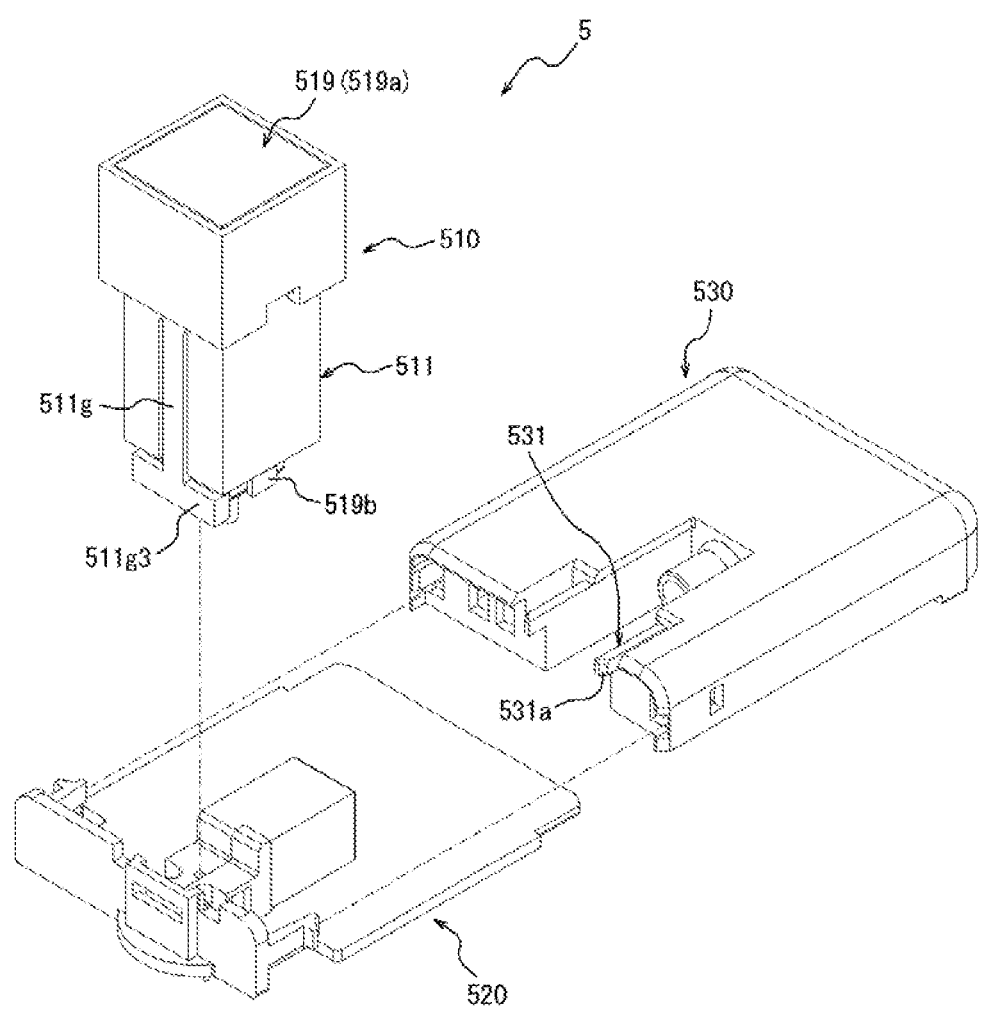
FIG. 17 is an exploded perspective view of a biological information detection device according to a fifth embodiment of the present disclosure.
Figure 18:
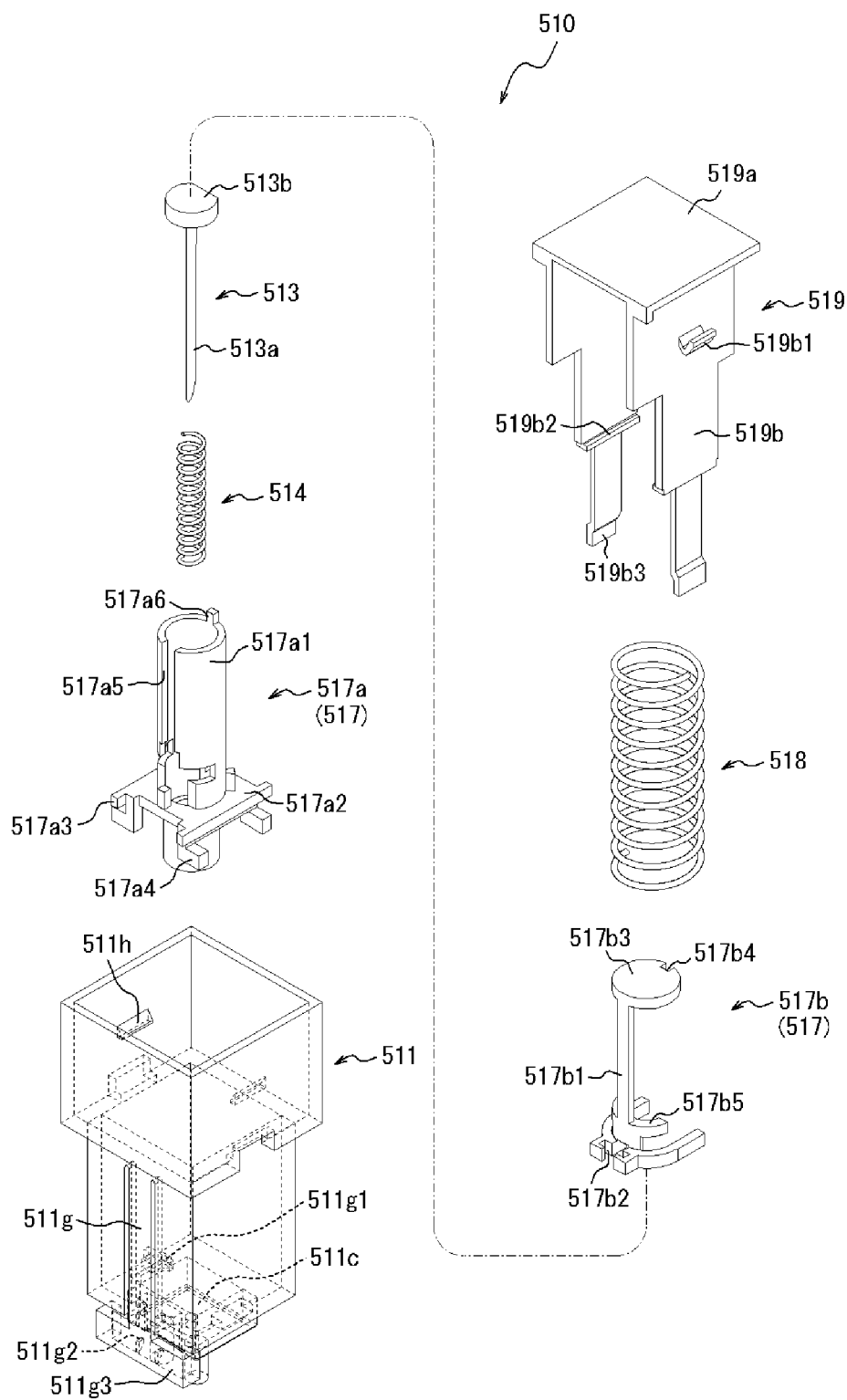
FIG. 18 is an exploded perspective view of a puncture unit of the biological information detection device of FIG. 17.

Specifically, the biological information detection device 5 according to the present embodiment includes: the puncture unit 510; the base member 520; and the detector 530 as illustrated in FIG. 17. In addition, the puncture unit 510 includes a housing 511, a slider 517a, a removing biasing member (a coil spring in this example) 514, a removing needle holding member 513, a lever member 517b, a puncturing biasing member (a coil spring in this example) 518, and a lid member 519 as illustrated in FIG. 18. Incidentally, the slider 517a and the lever member 517b constitute a puncturing needle holding member 517.

The housing 511 has a substantially rectangular parallelepiped shape with its upper side opened, and is provided with a through-hole, which allows the needle body 513a of the removing needle holding member 513 to penetrate therethrough, in a bottom wall 511c thereof. In addition, a lever body 511g is formed on a side wall on a front side of the housing 511. An engagement protrusion 511g1 capable of locking an engagement concave portion 517b2, provided on a front surface of a lever body 517b1 of the lever member 517b, is provided to protrude on a rear surface of a middle portion of the lever body 511g in the upper-lower direction. In addition, an engagement protrusion 511g2 for inhibiting detachment, which is locked by the base member 520 to inhibit detachment of the puncture unit 510 from the base member 520, is provided to protrude on a rear surface of a lower end portion of the lever body 511g of the housing 511. In addition, a pair of extension portions 511g3 protruding in the left-right direction are provided on the lower end portion of the lever body 511g.

The slider 517a includes a disk-shaped bottom wall having a through-hole through which the needle body 513a penetrates through at the center, and a substantially cylindrical peripheral wall 517a1 erected at a peripheral edge of the bottom wall. A flange portion 517a2 having a substantially rectangular shape in a top view is provided on a lower outer peripheral surface of the peripheral wall 517a1. Incidentally, a front-rear direction guide protrusions 517a3 guided by abutting on front and rear peripheral walls of the housing 511 when the slider 517a vertically moves inside the housing 511, and a left-right direction guide protrusions 517a4 guided by abutting on left and right peripheral walls of the housing 511 when the slider 517a vertically moves inside the housing 511 are provided at four corners of the flange portion 517a2.

A cut-out 517a5 housing the lever body 517b1 of the lever member 517b in a swingable manner is formed above the flange portion 517a2 in the peripheral wall 517a1 of the slider 517a. A fitting protrusion 517a6, fitted in a fitting concave portion 517b4 formed in a disk-shaped ceiling wall 517b3 of the lever member 517b, is provided in an upper end portion of the peripheral wall 517a1 of the slider 517a. The removing biasing member 514 is arranged between a bottom wall of the slider 517a and a substantially disk-shaped flange portion 513b of the removing needle holding member 513, and the lever member 517b is attached to the slider 517a in the state of housing the removing biasing member 514 and the removing needle holding member 513 therein. At the time of such attachment, an upper end edge of the flange portion 513b of the removing needle holding member 513 is locked by an engagement protrusion 517b5 provided in the lever body 517b1 of the lever member 517b in a state in which the removing biasing member 514 is compressed and deformed to cause the needle body 513a to protrude from the bottom wall of the slider 517a (see FIG. 19A).

As illustrated in FIG. 18, the lid member 519 includes a substantially rectangular ceiling plate 519a to close an upper opening of the housing 511, and a pair of left and right locking arms 519b hanging down from the ceiling plate 519a. Engagement pieces 519b1 to be locked by engagement protrusions 511h provided on the left and right peripheral walls of the housing 511 from above are provided on upper outer surfaces of the pair of locking arms 519b. In addition, engagement protrusions 519b2 capable of locking left and right end edges of the flange portion 517a2 of the slider 517a are provided on inner surfaces of the pair of locking arms 519b in a middle portion in the up-down direction. Receiving portions 519b3 capable of sliding contact with the outer surfaces of a pair of protruding portions 531 (see FIG. 17) provided at a front portion of the detector 530 are provided on inner surfaces of lower end portions of the pair of locking arms 519b. Front end portions of outer peripheral surfaces of the pair of protruding portions 531 are provided as inclined surfaces 531a inclined outward toward the rear side.

The puncturing biasing member 518 is arranged between the flange portion 517a2 of the puncturing needle holding member 517 and the ceiling plate 519a of the lid member 519, and the lid member 519 is attached to the housing 511 in a state in which the puncturing biasing member 518 and the puncturing needle holding member 517 are housed therein. At the time of such attachment, the flange portion 517a2 of the puncturing needle holding member 517 is locked by the engagement protrusions 519b2 of the pair of locking arms 519b in a state in which the puncturing biasing member 518 is compressed and deformed to move the puncturing needle holding member 517 upward (see FIG. 19C).

Figure 19A:
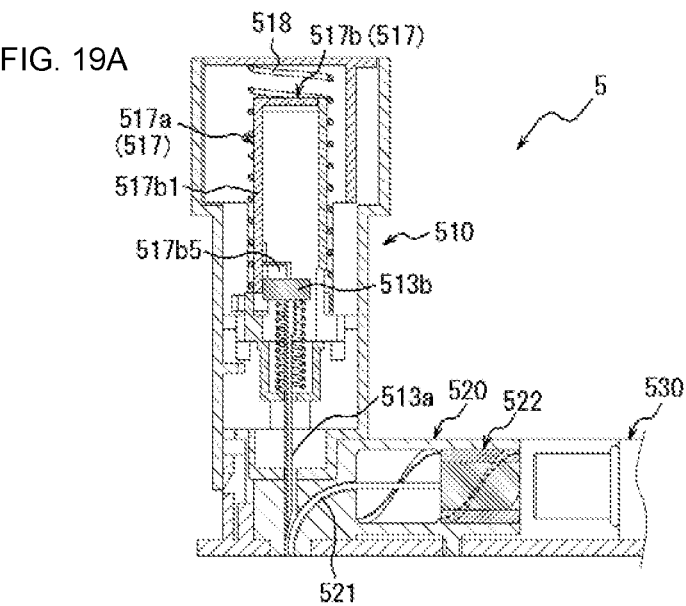
Figure 19B:
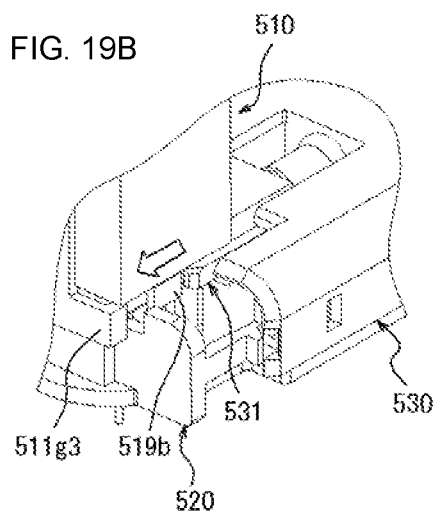
Figure 19C:
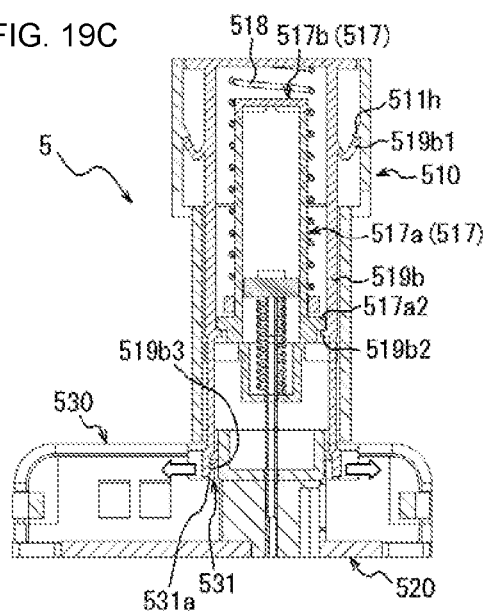

According to the biological information detection device 5 of the present embodiment configured in this manner, when the detector 530 is advanced in the state before puncture as illustrated in FIGS. 19A, 19B, and 19C, the pair of protruding portions 531 of the detector 530 advance as indicated by the arrow in FIG. 19B. Further, the inclined surfaces 531a provided at the front ends of the pair of protruding portions 531 abut on the receiving portions 519b3 of the pair of locking arms 519b to push and open that the pair of locking arms 519b as indicated by the arrow in FIG. 19C.

Figure 20A:
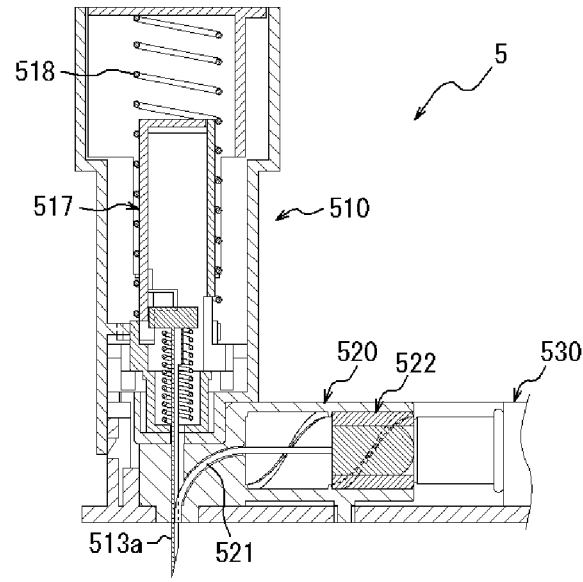
Figure 20B:
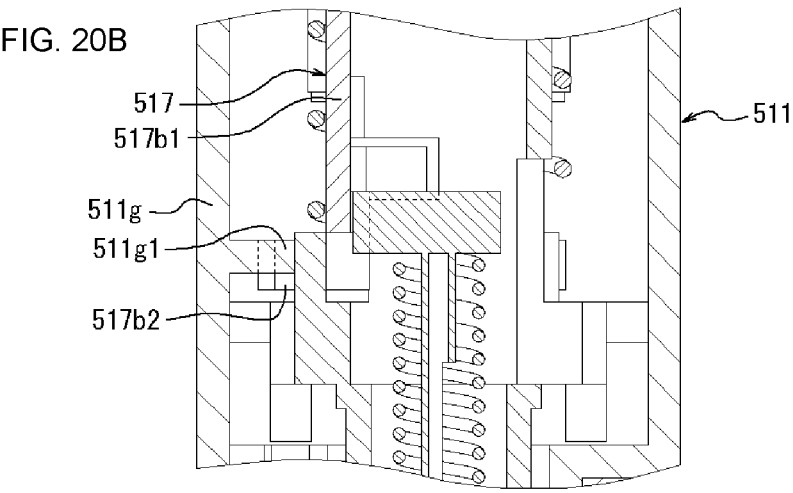

Then, the engagement between the engagement protrusions 519b2 of the pair of locking arms 519b and the flange portion 517a2 of the puncturing needle holding member 517 is released, and the puncturing needle holding member 517 is depressed by a downward biasing force of the puncturing biasing member 518, and the needle body 513a pierces the living body as illustrated in FIG. 20A. In addition, due to such depression, the engagement concave portion 517b2 of the lever body 517b1 of the puncturing needle holding member 517 is engaged with the engagement protrusion 511g1 of the lever body 511g of the housing 511 as illustrated in FIG. 20B.

Figure 21A:
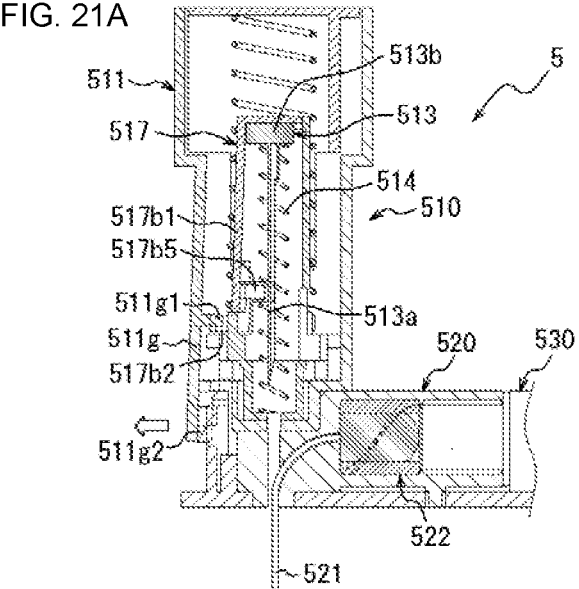
Figure 21B:
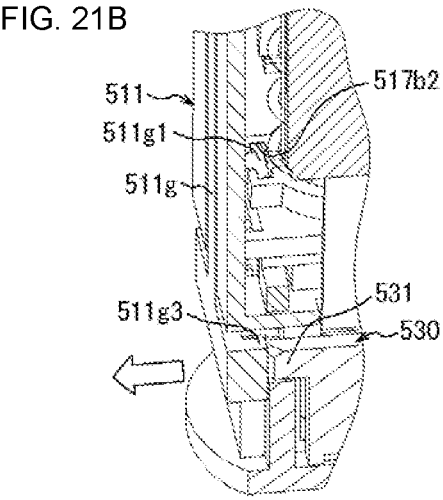
Figure 21C:
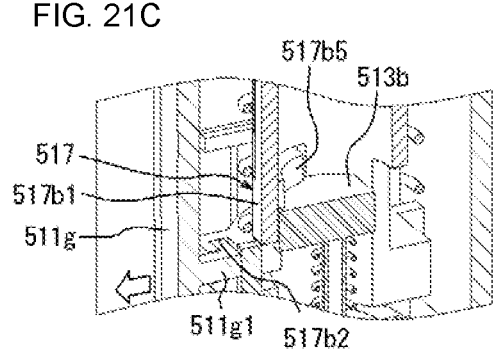
Figure 22A:
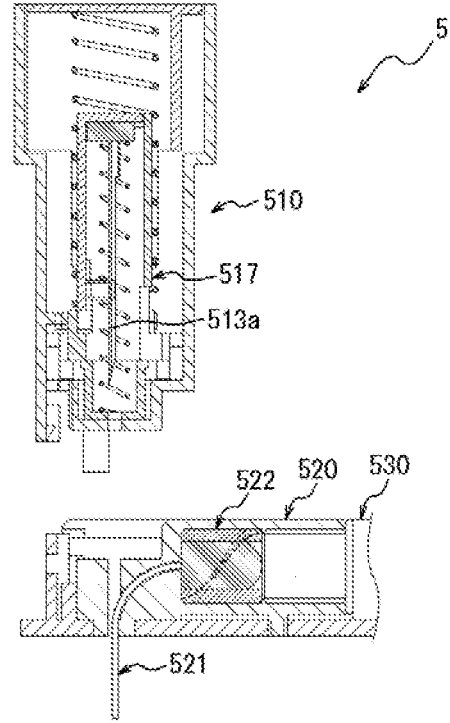
Figure 22B:
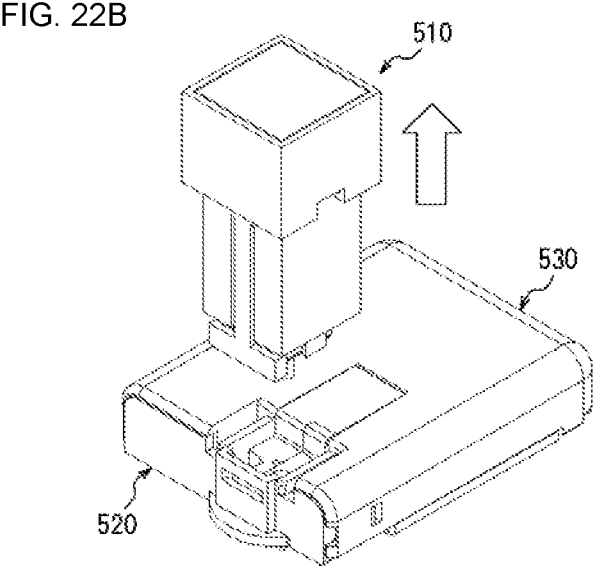

As the detector 530 is further advanced from this state, it is possible to push an end member 522 and insert a distal end portion of a sensor 521 into the living body. Then, when the insertion of the distal end portion of the sensor 521 into the living body is completed, the front end portions of the pair of protruding portions 531 of the detector 530 abut on a pair of extension portions 511g3 of the lever body 511g of the housing 511 to cause the lever body 511g to swing forward as illustrated in FIG. 21B. Due to such a swing of the lever body 511g, the lever body 517b1 of the puncturing needle holding member 517 engaged with the lever body 511g also swings forward as indicated by the arrow in FIG. 21C. As a result, the engagement between the flange portion 513b of the removing needle holding member 513 and the engagement protrusion 517b5 of the lever body 517b1 is released, and the removing needle holding member 513 moves upward by the biasing force of the removing biasing member 514, and the needle body 513a is removed from the living body as illustrated in FIG. 21A.

At this time, the engagement protrusion 511g2 between the engagement protrusion 511g2 for inhibiting detachment of the lever body 511g of the housing 511 and the base member 520 is released, and thus, the puncture unit 510 can be detached from the base member 520 as illustrated in FIG. 22. In addition, at the time of detaching the puncture unit 510, the needle body 513a is pulled into the puncturing needle holding member 517, and thus, it is possible to reduce the likelihood of a user contacting the needle body 513a.

In this manner, the biological information detection device 5 according to the present embodiment includes: the puncture unit 510 that holds the needle body 513a and is detachable from the base member 520, and is configured such that the needle body 513a pierces the living body by moving the detector 530 with respect to the base member 520, the end member 522 is pushed and moved by further moving the detector 530 so that the distal end portion of the sensor 521 is inserted into the living body along the needle body 513a, and the needle body 513a is removed from the living body and the puncture unit 510 can be detached from the base member 520 when the insertion of the distal end portion of the sensor 521 into the living body is completed.

Therefore, with the biological information detection device 5 according to the present embodiment, it is possible to realize the puncture of the needle body 513a, insertion of the sensor 521, removal of the needle body 513a, and enabling detachment of the puncture unit 510 through a series of operations of moving the detector 530, and thus, it is possible to make the operation remarkably easy.

In addition, the biological information detection device 5 according to the present embodiment includes: the puncturing needle holding member 517 that holds the needle body 513a; the puncturing biasing member 518 that biases the puncturing needle holding member 517 toward the surface of the living body; and the puncturing movable portion (the locking arm 519b) that is engaged with the puncturing needle holding member 517 to hold the state in which the puncturing needle holding member 517 receives the biasing force from the puncturing biasing member 518, and is configured such that the puncturing movable portion (the locking arm 519b) is released from engagement with the puncturing needle holding member 517 by being pushed by the detector 530 as the detector 530 is moved with respect to the base member 520.

In addition, the biological information detection device 5 according to the present embodiment includes: the removing needle holding member 513 that holds the needle body 513a; the removing biasing member 514 that biases the removing needle holding member 513 in the direction to be removed from the living body; and the removing movable portion (the lever body 511g and the lever body 517b1) that is engaged with the removing needle holding member 513 to hold the state in which the removing needle holding member 513 receives the biasing force from the removing biasing member 514, and is configured such that the removing movable portion (the lever body 511g and the lever body 517b1) is released from engagement with the removing needle holding member 513 by being pushed by the detector 530 when insertion of the distal end portion of the sensor 521 into the living body is completed.

Further, the biological information detection device 5 according to the present embodiment is configured such that the puncture unit 510 has the detachment-inhibiting movable portion (the lever body 511g) that is engaged with the base member 520 to inhibit detachment of the puncture unit 510 from the base member 520, and the detachment-inhibiting movable portion (the lever body 511g) is released from engagement with the base member 520 by being pushed by the detector 530 when insertion of the distal end portion of the sensor 521 into the living body is completed.

Therefore, with the biological information detection device 5 according to the present embodiment, it is possible to realize the remarkably easy operation with the simple configuration.

The above description merely illustrates one embodiment of the present disclosure, and various modifications can be made in the claims. For example, the optical sensor is used in the above-described embodiments, but the sensor is not limited to the optical type. For example, it is possible to use a sensor that detects end member biological information by transmitting an electrical signal corresponding to end member concentration of end member analyte to be detected, obtained by the sensor with a distal end portion indwelling inside end member living body, to the reception unit of the detector through an electrode provided at a proximal end portion of the sensor or the end member.

REFERENCE SIGNS LIST 1 to 5 biological information detection device
10 puncture unit
11 housing
11a upper opening
11b fitting convex portion
11c bottom wall
11d outer peripheral wall
11d1 engagement protrusion
11d2 inclined surface
11e detachment-inhibiting lever
11f engagement protrusion
12 button member
12a button
12b lower opening
12c inner peripheral wall
12d elastic arm
12e engagement protrusion
12f1 lower engagement protrusion
12f2 upper engagement protrusion
13 needle member
13a, 13aB needle body
13b flange portion
13c shaft
13d cylindrical wall
14 biasing member
15 cover
15a tube portion
15b engagement protrusion
20, 20B base member
20a fitting concave portion
20b engagement hole
20c bottom plate
20d vertical wall 20e engagement piece
20e1 engagement protrusion
20f base
20f1 through-hole
20f2, 20f2', 20f2", 20f2A end member guide path
20f3 screw thread (screw portion)
20f3' protrusion (screw portion)
20f4, 20f4B sensor guide path
20f5" screw groove (screw portion)
20f6B reversely curved guide portion
21, 21A, 21B sensor
21a measurement light emitting portion
21b light guide portion
22, 22', 22A end member
22a collimating lens (light adjustment portion)
22b inner tube
22b1, 22b1' screw groove (screw portion)
22b2" screw thread (screw portion)
30, 30A detector
30a engagement hole
30b, 30bA insertion tube portion
30b1A operation portion
210 puncture unit
211 housing
211c bottom wall
211c1 slot
213 puncturing needle holding member
213a needle body
213b flange portion
214 puncturing biasing member
216 lever member (puncturing movable portion)
216a swing shaft
216b lever main body
216c engagement protrusion
220 base member
221 sensor
222 end member
230 detector
310 puncture unit
311e detachment-inhibiting lever (detachment-inhibiting movable portion)
311e1 extension portion
311f engagement protrusion
313a needle body
320 base member
320b engagement hole
320d vertical wall
321 sensor
330 detector
410 puncture unit
411 housing
411c bottom wall
411g lever body (removing movable portion)
411g1 engagement protrusion
411g2 engagement protrusion
411g3 extension portion
413 removing needle holding member
413a needle body
413b flange portion
413e depressing operation portion
414 removing biasing member
420 base member
421 sensor
430 detector
510 puncture unit
511 housing
511c bottom wall
511g lever body (removing movable portion, detachment-inhibiting movable portion)
511g1 engagement protrusion
511g2 engagement protrusion
511g3 extension portion
511h engagement protrusion
513 removing needle holding member
513a needle body
513b flange portion
514 removing biasing member
517 puncturing needle holding member
517a slider
517a1 peripheral wall
517a2 flange portion
517a3 front-rear direction guide protrusion
517a4 left-right direction guide protrusion
517a5 notch
517a6 fitting protrusion
517b lever member
517b1 lever body (removing movable portion)
517b2 engagement concave portion
517b3 ceiling wall
517b4 fitting concave portion
517b5 engagement protrusion
518 puncturing biasing member
519 lid member
519a ceiling board
519b locking arm (puncturing movable portion)
519b1 engagement piece
519b2 engagement protrusion
519b3 receiving portion
520 base member
521 sensor
522 end member
530 detector
531 protruding portion
531a inclined surface
S screw portion
F fitting portion

What is claimed is:

1. A biological information detection device comprising:
a needle body configured to pierce the living body;
a sensor that has an elongated shape and that includes:
 a proximal end portion that is movable in a direction different from an extending direction of the needle body, and
 a distal end portion that is insertable into the living body by moving along the needle body after the needle body has pierced the living body, and that is configured to indwell inside the living body,
 wherein the sensor is configured to detect biological information using the distal end portion;
an end member that is fixed to the proximal end portion of the sensor and that has a first cylindrical outer peripheral surface, wherein the end member is configured to pass a signal obtained from the sensor therethrough, the signal containing information indicative of a concentration of an analyte to be detected;
a base member that is affixable to a surface of the living body;
an end member guide path that is located in the base member and that has a cylindrical inner peripheral surface, wherein the end member guide path is configured to accommodate and guide the end member; and
a detector configured to receive the signal from the end member, and to detect the concentration of the analyte to be detected based on the received signal, wherein the detector is attachable to and detachable from the base member and comprises:
  an insertion tube portion having a second cylindrical outer peripheral surface, the insertion tube portion being insertable into the end member guide path, and
  an operation portion that is integrally rotatable with the insertion tube portion,
wherein the end member is configured to rotate as the end member is pushed and moved by the detector, and
wherein the distal end portion of the sensor is configured to move along the needle body as the end member is pushed and moved by the detector,
wherein the inner peripheral surface of the end member guide path and the second cylindrical outer peripheral surface of the insertion tube portion are connectable via a screw portion that is configured to move the insertion tube portion in a depth direction of the end member guide path in accordance with a rotational operation of the operation portion, and
wherein a distal end surface of the insertion tube portion and a proximal end surface of the end member are connectable via a fitting portion that inhibits mutual rotation.

2. The biological information detection device according to claim 1, wherein the proximal end portion of the sensor is movable in a direction along a surface of the living body.

3. The biological information detection device according to claim 1, wherein the sensor comprises:
  a measurement light emitting portion that is located at the distal end portion of the sensor and is configured to emit light, and
  a light guide portion configured to transmit the light from the measurement light emitting portion to a proximal end portion of the sensor.

4. The biological information detection device according to claim 3, wherein the end member comprises a light adjustment portion configured to collect light diffused from the proximal end portion of the sensor.

5. The biological information detection device according to claim 4, wherein the light adjustment portion is configured to collect the light diffused from the proximal end portion of the sensor so as to become collimated light.

6. The biological information detection device according to claim 1, wherein:
  the base member comprises a sensor guide path configured to guide the sensor,
  the sensor guide path comprises:
    a curved guide portion that is curved toward the surface of the living body in a direction approaching the needle body, and
    a reversely curved guide portion configured to guide the sensor to curve in a direction opposite from a direction in which the curved guide portion is curved, the reversely curved guide portion being located on a needle body side with respect to the curved guide portion.

7. The biological information detection device according to claim 1, wherein:
  the needle body is configured to pierce the living body as the detector is moved with respect to the base member.

8. The biological information detection device according to claim 7, further comprising:
  a puncturing needle holding member that holds the needle body;
  a puncturing biasing member that provides a biasing force to the puncturing needle holding member toward the surface of the living body; and
  a puncturing movable portion that is engaged with the puncturing needle holding member to hold a state in which the puncturing needle holding member receives the biasing force from the puncturing biasing member,
  wherein the puncturing movable portion is configured to be released from engagement with the puncturing needle holding member by being pushed by the detector as the detector is moved with respect to the base member.

9. The biological information detection device according to claim 1, further comprising a puncture unit that holds the needle body and is detachable from the base member by the detector being moved with respect to the base member when insertion of the distal end portion of the sensor into the living body is completed.

10. The biological information detection device according to claim 9, wherein:
  the puncture unit further comprises a detachment-inhibiting movable portion that is engaged with the base member to inhibit detachment of the puncture unit from the base member, and
  the detachment-inhibiting movable portion is configured to be released from engagement with the base member by being pushed by the detector when insertion of the distal end portion of the sensor into the living body is completed.

11. The biological information detection device according to claim 1, wherein the needle body is configured to be removed from the living body when the detector is moved with respect to the base member and insertion of the distal end portion of the sensor into the living body is completed.

12. The biological information detection device according to claim 11, further comprising:
  a removing needle holding member that holds the needle body;
  a removing biasing member that provides a biasing force to the removing needle holding member in a direction away from the surface of the living body; and
  a removing movable portion that is engaged with the removing needle holding member to hold a state in which the removing needle holding member receives the biasing force from the removing biasing member,
  wherein the removing movable portion is configured to be released from engagement with the removing needle holding member by being pushed by the detector when insertion of the distal end portion of the sensor into the living body is completed.

13. A biological information detection device comprising:
  a needle body configured to pierce the living body;
  a puncturing needle holding member that holds the needle body;
  a puncturing biasing member that provides a biasing force to the puncturing needle holding member toward the surface of the living body;
  a puncturing movable portion that is engaged with the puncturing needle holding member to hold a state in which the puncturing needle holding member receives the biasing force from the puncturing biasing member;
  a sensor that has an elongated shape and that includes:
    a proximal end portion that is movable in a direction different from an extending direction of the needle body, and
    a distal end portion that is insertable into the living body by moving along the needle body after the needle body has pierced the living body, and that is configured to indwell inside the living body, wherein the sensor is configured to detect biological information using the distal end portion;

an end member that is fixed to the proximal end portion of the sensor and that is configured to pass a signal obtained from the sensor therethrough, the signal containing information indicative of a concentration of an analyte to be detected;

a base member that is affixable to a surface of the living body; an end member guide path that is located in the base member and is configured to guide the end member; and a detector configured to receive the signal from the end member, and to detect the concentration of the analyte to be detected based on the received signal, wherein the detector is attachable to and detachable from the base member, wherein the distal end portion of the sensor is configured to move along the needle body when the end member is pushed and moved by the detector, wherein the puncturing movable portion is configured to be released from engagement with the puncturing needle holding member by being pushed by the detector, and thereby cause the needle body to pierce the living body, as the detector is moved with respect to the base member, and wherein the distal end portion of the sensor is configured to move along the needle body as the end member is pushed and moved by the detector.

14. A biological information detection device comprising:

a needle body configured to pierce the living body;

a removing needle holding member that holds the needle body;

a removing biasing member that provides a biasing force to the removing needle holding member in a direction away from the surface of the living body;

a removing movable portion that is engaged with the removing needle holding member to hold a state in which the removing needle holding member receives the biasing force from the removing biasing member;

a sensor that has an elongated shape and that includes:

a proximal end portion that is movable in a direction different from an extending direction of the needle body, and a distal end portion that is insertable into the living body by moving along the needle body after the needle body has pierced the living body, and that is configured to indwell inside the living body, wherein the sensor is configured to detect biological information using the distal end portion;

an end member that is fixed to the proximal end portion of the sensor and that is configured to pass a signal obtained from the sensor therethrough, the signal containing information indicative of a concentration of an analyte to be detected;

a base member that is affixable to a surface of the living body;

an end member guide path that is located in the base member and is configured to guide the end member; and a detector configured to receive the signal from the end member, and to detect the concentration of the analyte to be detected based on the received signal, wherein the detector is attachable to and detachable from the base member, wherein the removing movable portion is configured to be released from engagement with the removing needle holding member by being pushed by the detector, and thereby cause the needle body to be removed from the living body, when the detector is moved with respect to the base member and insertion of the distal end portion of the sensor into the living body is completed.

* * * * *